United States Patent
Schöb et al.

(10) Patent No.: US 10,873,241 B2
(45) Date of Patent: Dec. 22, 2020

(54) ELECTROMAGNETIC ROTARY DRIVE

(71) Applicant: Levitronix GmbH, Zürich (CH)

(72) Inventors: Reto Schöb, Rudolfstetten (CH); Jörg Hugel, Zürich (CH); Thomas Holenstein, Umiken (CH)

(73) Assignee: LEVITRONIX GMBH, Zurich (CH)

( * ) Notice: Subject to any disclaimer, the term of this patent is extended or adjusted under 35 U.S.C. 154(b) by 468 days.

(21) Appl. No.: 15/177,764

(22) Filed: Jun. 9, 2016

(65) Prior Publication Data

US 2017/0012491 A1    Jan. 12, 2017

(30) Foreign Application Priority Data

Jul. 6, 2015 (EP) ..................... 15175531

(51) Int. Cl.
*H02K 7/09* (2006.01)
*F04D 29/058* (2006.01)
(Continued)

(52) U.S. Cl.
CPC ............ *H02K 7/09* (2013.01); *A61M 1/1015* (2014.02); *A61M 1/1031* (2014.02);
(Continued)

(58) Field of Classification Search
CPC ...... H02K 7/09; H02K 21/028; H02K 19/103; H02K 1/146; H02K 1/17; H02K 1/22;
(Continued)

(56) References Cited

U.S. PATENT DOCUMENTS

| | | | | | |
|---|---|---|---|---|---|
| 3,877,761 | A | * | 4/1975 | Boden | F16C 32/0474 310/90.5 |
| 4,732,353 | A | * | 3/1988 | Studer | B64G 1/28 244/165 |
| 5,111,102 | A | * | 5/1992 | Meeks | F16C 32/0444 310/90.5 |
| 6,130,494 | A | * | 10/2000 | Schob | F16C 32/0463 310/90.5 |

(Continued)

FOREIGN PATENT DOCUMENTS

| | | | | |
|---|---|---|---|---|
| EP | 0899855 A1 | | 3/1999 | |
| EP | 1028262 A1 | * | 8/2000 | .......... F16C 32/0465 |

(Continued)

OTHER PUBLICATIONS

Extended European Search Report dated Jan. 15, 2016 in EP Patent Application 15175531.1, filed Jul. 6, 2015.

*Primary Examiner* — Edgardo San Martin
(74) *Attorney, Agent, or Firm* — Global IP Counselors, LLP

(57) ABSTRACT

An electromagnetic rotary drive includes a magnetically contactlessly drivable rotor free of coils, and a stator configured as a bearing and drive stator configured to drive the rotor magnetically and contactlessly about an axis of rotation. The rotor is capable of being supported magnetically contactlessly with respect to the stator in an operating state. The stator includes an upper stator part having a plurality of pronounced upper poles configured to carry upper windings and a lower stator part having a plurality of pronounced lower poles configured to carry lower windings. The upper stator part and the lower stator part are arranged spaced apart from one another with respect to an axial direction. A permanent magnet is disposed between the upper stator part and the lower stator part.

16 Claims, 26 Drawing Sheets

(51) Int. Cl.

| | |
|---|---|
| *F04D 29/048* | (2006.01) |
| *H02K 19/10* | (2006.01) |
| *H02K 1/14* | (2006.01) |
| *H02K 1/17* | (2006.01) |
| *H02K 1/22* | (2006.01) |
| *H02K 3/18* | (2006.01) |
| *A61M 1/10* | (2006.01) |
| *F16C 32/04* | (2006.01) |
| *F04D 3/00* | (2006.01) |
| *F04D 13/06* | (2006.01) |
| *F04D 25/06* | (2006.01) |
| *B01F 13/08* | (2006.01) |
| *A61M 1/12* | (2006.01) |

(52) U.S. Cl.
CPC ....... *A61M 1/1086* (2013.01); *B01F 13/0872* (2013.01); *F04D 3/00* (2013.01); *F04D 13/0673* (2013.01); *F04D 25/0613* (2013.01); *F04D 29/048* (2013.01); *F04D 29/058* (2013.01); *F16C 32/0446* (2013.01); *F16C 32/0457* (2013.01); *F16C 32/0465* (2013.01); *F16C 32/0485* (2013.01); *H02K 1/146* (2013.01); *H02K 1/17* (2013.01); *H02K 1/22* (2013.01); *H02K 3/18* (2013.01); *H02K 19/103* (2013.01); *A61M 1/101* (2013.01); *A61M 1/1012* (2014.02); *A61M 1/12* (2013.01); *F16C 32/0489* (2013.01)

(58) Field of Classification Search
CPC ....... H02K 3/18; F04D 29/058; F04D 29/048; F04D 3/00; F04D 13/0673; F04D 25/0613; F04D 25/0646; F16C 32/0465; A61M 1/1015

See application file for complete search history.

(56) References Cited

U.S. PATENT DOCUMENTS

| | | | | |
|---|---|---|---|---|
| 6,181,040 | B1 * | 1/2001 | Schob | F16C 32/0493 310/103 |
| 6,297,574 | B1 * | 10/2001 | Schob | F16C 32/0453 310/168 |
| 6,365,996 | B2 * | 4/2002 | Schob | F16C 32/0463 310/90.5 |
| 6,559,567 | B2 * | 5/2003 | Schob | F16C 32/0444 310/156.01 |
| 6,637,433 | B2 * | 10/2003 | Schob | A61M 16/0057 128/204.19 |
| 7,112,903 | B1 * | 9/2006 | Schob | F16C 32/0465 310/90.5 |
| 7,832,922 | B2 * | 11/2010 | Schoeb | B01F 7/00716 366/273 |
| 9,835,158 | B2 * | 12/2017 | Schob | F04D 1/006 |
| 2001/0013734 | A1 * | 8/2001 | Kanebako | F16C 32/0493 310/90.5 |
| 2003/0057784 | A1 * | 3/2003 | Kanebako | F16C 32/0493 310/90.5 |
| 2004/0135450 | A1 * | 7/2004 | Kanebako | G11B 19/2009 310/90.5 |
| 2005/0226746 | A1 * | 10/2005 | Schob | B24B 37/04 417/423.15 |
| 2007/0152529 | A1 * | 7/2007 | Kamiya | B60L 9/18 310/166 |
| 2009/0121571 | A1 | 5/2009 | Onuma | |
| 2013/0207504 | A1 | 8/2013 | Park et al. | |
| 2014/0062239 | A1 * | 3/2014 | Schoeb | H02K 7/09 310/90.5 |
| 2017/0007973 | A1 * | 1/2017 | Schob | B01F 13/0854 |
| 2017/0302145 | A1 * | 10/2017 | Holenstein | H02K 19/103 |

FOREIGN PATENT DOCUMENTS

| | | | |
|---|---|---|---|
| EP | 1814212 A1 | 8/2007 | |
| JP | 2000-184655 A | 6/2000 | |
| JP | 2000184655 A * | 6/2000 | ......... F16C 32/0465 |
| JP | 2014209832 A | 11/2014 | |

* cited by examiner

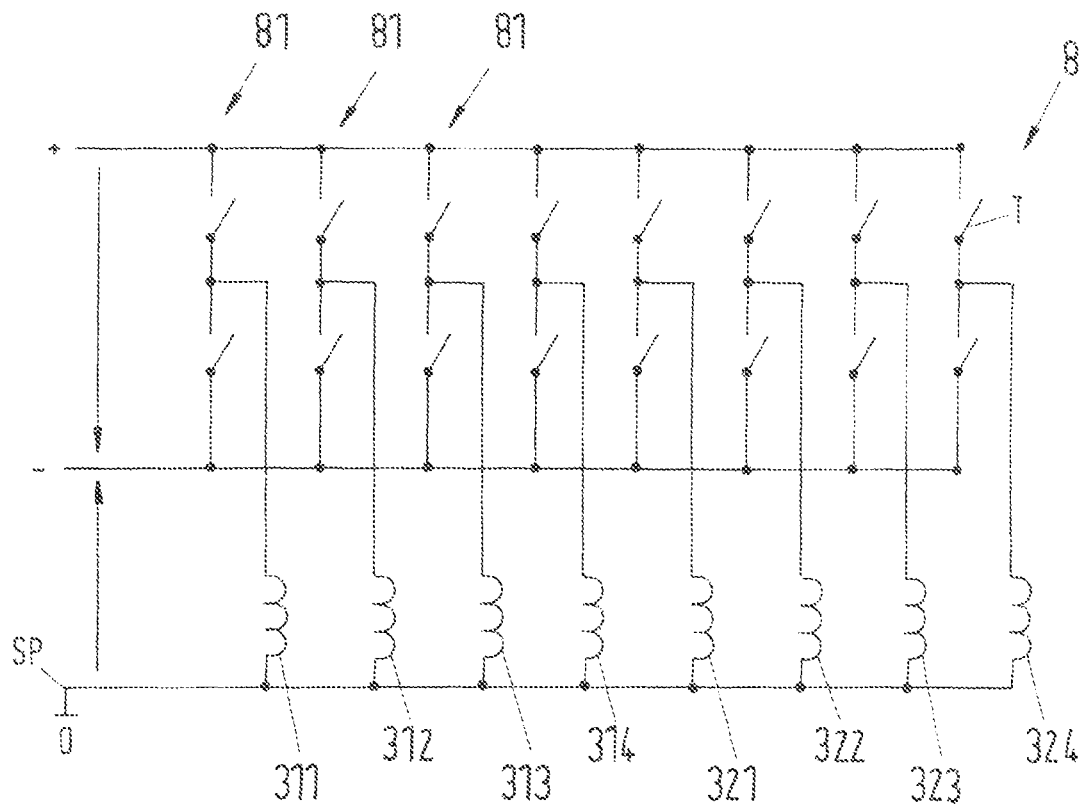

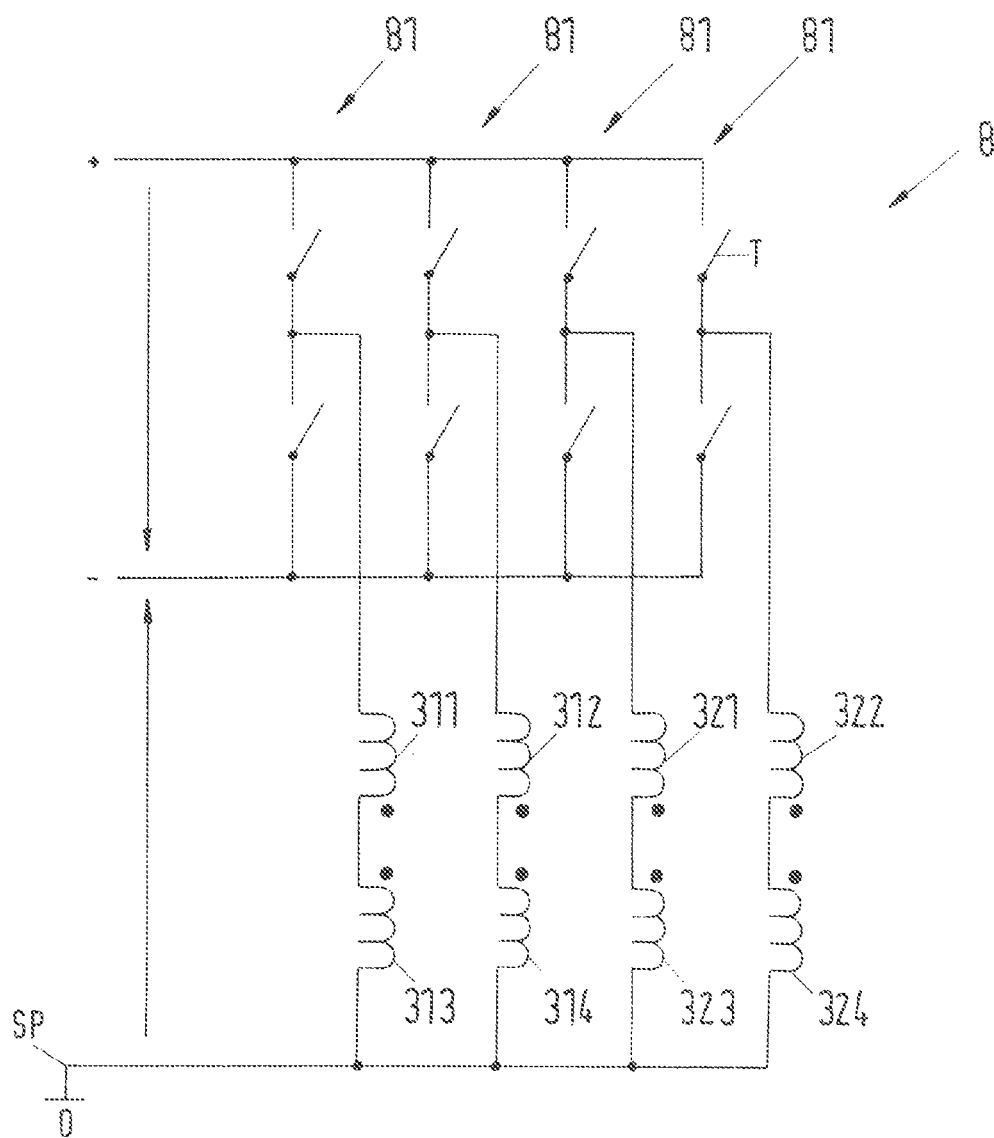

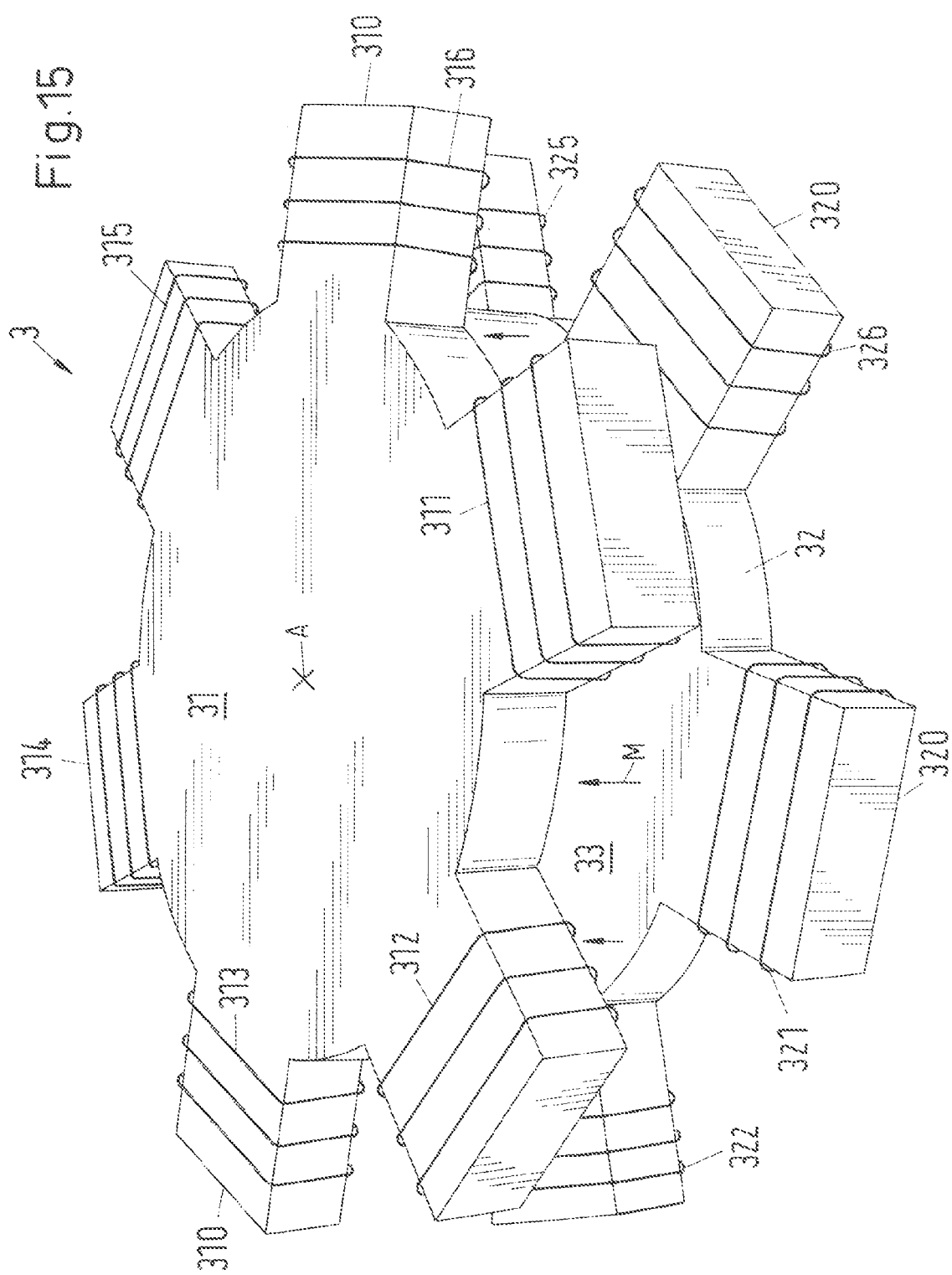

ELECTROMAGNETIC ROTARY DRIVE

CROSS-REFERENCE TO RELATED APPLICATIONS

This application claims priority to EP Application No.: 15175531.1, filed Jul. 6, 2015, the contents of which is hereby incorporated herein by reference.

BACKGROUND

Field of the Invention

The invention relates to an electromagnetic rotary drive.

Background of the Invention

Electromagnetic rotary drives are known which are configured and operated in accordance with the principle of a bearingless motor. The term bearingless motor in this respect means an electromagnetic rotary drive in which the rotor is supported completely magnetically with respect to the stator, with no separate magnetic bearings being provided. For this purpose, the stator is configured as a bearing and drive stator which is therefore both the stator of the electric drive and the stator of the magnetic support. A rotating magnetic field can be produced using the electrical windings which, on the one hand, exerts a torque onto the rotor which effects its rotation and which, on the other hand, exerts a shear force, which can be set as desired, onto the rotor so that the rotor's radial position can be controlled or regulated actively. The absence of a separate magnetic bearing with a complete magnetic support of the rotor is the property which gives the bearingless motor its name.

SUMMARY

The bearingless motor has become sufficiently well-known to the skilled person in the meantime and is used for a number of different applications. Some fundamental descriptions can be found, for example, in EP-A-0 860 046 and EP-A-0 819 330.

Due to the absence of mechanical bearings, the bearingless motor is in particular suitable for pumping and mixing apparatus with which very sensitive substances are conveyed, for example blood pumps, or on which very high demands are made on purity, for example in the pharmaceutical industry or in the biotechnological industry, or with which abrasive substances are conveyed which would very quickly destroy mechanical bearings, for example pumps or mixers for slurry in the semiconductor industry. Bearingless motors are also used in semiconductor production for supporting and rotating wafers, for example when they are coated with photoresist or other substances.

A further advantage of the principle of the bearingless motor in pumping or mixing applications results from the design of the rotor as an integral rotor which is both the rotor of the electromagnetic drive and the rotor of the pump or mixer. In addition to the contactless magnetic support, the advantage results here of a very compact and space-saving configuration.

In addition, the principle of the bearingless motor also allows designs in which the rotor can be very easily separated from the stator. This is a very big advantage since the rotor can thus be designed as a single-use part for single use, for example. Such single-use applications today frequently replace processes in which all those components which come into contact with the substances to be treated in the process once had to be cleaned and sterilized in a complex and/or expensive manner, for example by means of steam sterilization, due to the very high purity demands. In the configuration for single use, those components which come into contact with the substances to be treated are only used exactly once and are then replaced with new, that is unused, single-use parts in the next application.

The pharmaceutical industry and the biotechnological industry can be named as examples here. Solutions and suspensions are frequently produced here which require a careful blending or conveying of the substances.

In the pharmaceutical industry, for example in the production of pharmaceutically active substances, very high demands are made on cleanliness; the components which come into contact with the substances often even have to be sterile. Similar demands also result in biotechnology, for example in the manufacture, treatment or cultivation of biological substances, cells or microorganisms, where an extremely high degree of cleanliness has to be ensured in order not to endanger the usability of the product produced. Bioreactors can be named as a further example here in which, for example, biological substitutes for tissue or special cells or other very sensitive substances are cultivated. Pumping or mixing apparatus are also required here in order, for example, to ensure a continuous blending of the nutrient fluid or to ensure its continuous circulation in the mixing tank. A very high purity has to be ensured in this respect to protect substances or the produced products from contamination. In such applications, the pumping or mixing apparatus is then composed of a single-use apparatus and a reusable apparatus. In this respect, the single-use apparatus comprises those components which come into contact with the substances and which are configured as single-use parts for single use. This is, for example, the pumping or mixing tank with the rotor which is provided therein and which then, for example, comprises an impeller for conveying the substances. The reusable apparatus comprises those components which are used permanently, that is multiple times, for example the stator. Such an apparatus is disclosed, for example, in EP-B-2 065 085.

In the configuration as a single-use part, the pumping or mixing tank is frequently designed as a flexible plastic pouch or as a plastic sack with a rotor contained therein. These pouches are frequently already sterilized during manufacture or after the packaging and storing and are supplied to the customer in sterile form in the packaging.

It is an important criterion for the manufacture or design of single-use parts for single use that they can be assembled in as simple a manner as possible with the reusable apparatus or its components. It is desirable that this assembly can take place with as little effort as possible, with little work, fast and preferably without tools.

Another aspect is that these single-use parts can be manufactured as economically and inexpensively as possible. In this respect value is in particular also placed on reasonably priced, simple starting materials such as commercial plastics. An environmentally aware handling and a responsible use of the available resources are also major aspects in the design of disposable parts.

Such configurations are also known in which the total pumping or mixing apparatus is configured for single use.

Starting from this prior art, it is an object of the invention to provide another electromagnetic rotary drive which is configured according to the principle of the bearingless motor and which can be used for a plurality of applications. The rotary drive should furthermore also be able to be configured for applications using components for single use. The subject of the invention satisfying this object is characterized by the features described herein.

In accordance with the invention, an electromagnetic rotary drive is therefore proposed having a rotor which can be magnetically contactlessly driven and which is configured as free of coils, and having a stator which is configured as a bearing and drive stator with which the rotor can be driven magnetically contactlessly about a desired axis of rotation in the operating state and can be supported magnetically contactlessly with respect to the stator, with the stator comprising an upper stator part having a plurality of pronounced upper poles for carrying upper poles and a lower stator part having a plurality of pronounced lower poles for carrying lower windings, wherein the upper stator part and the lower stator part are arranged spaced apart from one another with respect to the axial direction and wherein a permanent magnet is provided between the upper stator part and the lower stator part.

It is possible by the specific configuration of the stator, which comprises a permanent magnet, to generate a very large proportion of the magnetic flux or even to generate the total magnetic flux in the stator. It in particular hereby becomes possible that the rotor only contributes a little, if anything, to the generation of the magnetic flux, but rather only has to conduct or guide it. It is thus possible to dispense with strong permanent magnets or magnetically very hard materials.

It is customary in accordance with today's prior art in particular to use metals of the rare earths or compounds or alloys of these metals as permanent magnets in the rotor because very strong permanent magnetic fields can be generated using them due to their magnetic properties. Known and frequently used examples of these rare earths are neodymium and samarium. However, such metals represent a substantial cost factor due to their comparatively small occurrence and due to their complex and/or expensive mining and processing. In addition, the waste disposal of such permanent magnets after a single use, for example, is frequently also associated with problems or a high effort under technical environmental aspects, whereby additional costs arise. It is therefore advantageous under economic, cost and environmental aspects, in particular also in single-use applications, that the invention makes it possible in particular to dispense with such permanent magnet materials consisting of or comprising rare earths in the rotors.

The rotor preferably comprises a magnetically active core and is free of permanent magnets. The rotor can be produced particularly simply, economically and inexpensively due to the complete omission of permanent magnets in the rotor, which in particular also represents a huge advantage for an embodiment as a single-use rotor. Depending on the configuration, different jackets, gaps and walls, in particular a jacket of the magnetically active core, the fluid gap or a separating can which surrounds the stator, are accommodated in the region between the stator and the magnetically active core of the rotor. In order to accommodate all these elements, a spacing of at least 3 mm, preferably 4-6 millimeters, is preferred between the stator and the magnetically active core of the rotor. Since the rotor of the electromagnetic rotary drive in accordance with the invention should preferably not have any permanent magnets and thus cannot contribute to the magnetomotive force, the total magnetomotive force has to be produced in the stator. For a spacing of, for example, 3 millimeters between the stator and the magnetically active core of the rotor, a magnetomotive force of around 5000 amperes is necessary to be able to support and drive the rotor in an active magnetic manner. If the stator is excited as customary solely by windings, such a high magnetomotive force is impossible to realize in the mostly tight construction space of the stator with reasonable dimensions. In accordance with the invention, one or more permanent magnets are therefore attached in the stator which generate a constant premagnetization flux. However, since neither a rotating field for generating a toque nor a regulable magnetic flux for the active magnetic support of the rotor can be generated with a constant magnetic flux, coils are additionally attached in the stator by which additional electromagnetic magnetic fluxes are produced which are thus variable and regulable. In this respect, the electromagnetic flux paths are conducted such that they do not lead through the permanent magnet or permanent magnets. Most permanent magnets, in particular rare earth magnets, but also ferrite magnets, have a relative permeability which is only insignificantly above one. If the electromagnetic flux paths were therefore to lead through the permanent magnet or permanent magnets, the electromagnetically active air gap would thus increase by the construction height of the permanent magnets located in the flux path and would additionally increase the magnetomotive force requirement. It is thus also an essential aspect of the invention that the permanent magnetically excited fluxes and the electromagnetically excited fluxes can be guided so that they superpose in the magnetic air gap between the stator and the rotor, but are conducted separately in the region of the permanent magnets. The electromagnetically excited fluxes should preferably be conducted, where possible, through magnetically soft material such as iron or silicon iron in addition to the region of the air gaps between the rotor and the stator. The air gap fluxes can be modulated by the superposition of the permanent magnetically excited fluxes and of the electromagnetically excited fluxes in the region of the air gaps between the rotor and the stator such that both a regulation of the radial rotor position and the forming of tangential force components, which effect a torque, are made possible.

It is advantageous with respect to the stator if the upper stator part or the lower stator part comprises exactly three or exactly four or exactly six upper and lower poles. The embodiment with three poles has the advantage that it in particular leaves a particularly large amount of space for the coils or for the windings of the stator in embodiments of the rotor and stator as external rotors at the poles of the stator. This embodiment additionally allows a particularly high electromagnetic magnetomotive force. The embodiment with four poles has the advantage that it allows a particularly symmetrical arrangement of the poles, which is particularly favorable from a technical control or regulation aspect. The embodiment with six poles is advantageous because it allows a particularly favorable and homogeneous generation of the torque and of the shear force on the rotor.

It is preferred if the number of the upper poles is the same as the number of lower poles. This allows a particularly simple manufacturing process and additionally simplifies the electrical control and the regulation of the apparatus.

A further advantageous embodiment comprises the upper stator part and the lower stator part being arranged rotated by an angle toward one another with respect to the desired axis of rotation so that, viewed in the axial direction, the upper poles are each arranged in a gap between two adjacent lower poles, with the angle preferably amounting to 360° divided by the total number of upper and lower poles. It can be ensured particularly well by this measure that a torque can be generated on the rotor by the one of the two stator parts, while simultaneously a resulting shear force can be generated on the rotor in the radial direction by the other stator part.

In a further preferred embodiment, the number of upper poles and the number of lower poles is an even number, with the upper poles and the lower poles being arranged such that they overlap viewed in an axial direction. The rotor can also be actively magnetically regulated by this measure with respect to tilts against the desired axis of rotation (two degrees of freedom).

A further preferred embodiment is characterized in that the rotor comprises at least one impeller for conveying fluids. The rotor of the electromagnetic rotary drive can thus simultaneously be the rotor of a pumping or mixing apparatus.

It is another preferred embodiment that at least two separate rotors are provided of which each is respectively magnetically contactlessly drivable and is respectively designed as free of coils, wherein the rotors are arranged spaced apart from one another and coaxially with respect to the axial direction in the operating state and at least two stators are provided of which each is configured as a bearing and drive stator, wherein each stator respectively comprises an upper stator part having a plurality of pronounced upper poles for carrying upper windings and a lower stator part having a plurality of pronounced lower poles for carrying lower windings, wherein the upper stator part and the lower stator part of each stator are arranged spaced apart from one another with respect to the axial direction, wherein a permanent magnet is respectively provided between the upper stator part and the lower stator part, and wherein the two stators are arranged spaced apart from one another with respect to the axial direction in the operating state. This embodiment with at least two stators and with at least two rotors allows operating states, for example in mixing or pumping apparatus, in which the two rotors rotate in opposite directions and/or at different speeds. In this respect, a separate stator is associated with each rotor and drives this rotor contactlessly and simultaneously supports it magnetically contactlessly.

It is an advantageous measure that the magnetically active core of the rotor has a plurality of pronounced rotor poles which face the poles of the stator in the operating state. A particularly good and efficient guidance of the magnetic flux can hereby be ensured.

In this respect, depending on the embodiment, it is a preferred measure for the rotor poles to be configured or arranged so asymmetrically that positions of engagement are avoided with respect to the stator in the operating state. This asymmetry is particularly suitable if the stator comprises a relatively small number of poles, for example a respective three or four upper and lower poles. There are a number of possibilities to realize the asymmetry; for example, the symmetry between the rotor poles and the poles of the stator can be broken by the length of the rotor poles measured in the peripheral direction or by the angular spacing of the rotor poles. Such relative rotary positions between the rotor and the stator should be avoided by this measure in which it is no longer possible, due to the symmetry, to exert a resulting torque on the rotor by the stator, that is in which the rotor engages when standing still.

It is a further advantageous measure that the magnetically active core of the rotor has a ring-shaped design, with a peripheral ring of constant diameter being formed at the center with respect to the axial direction and with the rotor poles being provided above and below the ring. The number of the position sensors in the stator can be reduced by this measure with which the radial position of the rotor relative to the stator is determined.

It is preferred for the generation of the electromagnetic fields or of the rotating fields that a coil is arranged as a winding on each upper stator pole and at each lower stator pole, wherein a respective separate power amplifier is provided for each coil with which the coil current or the coil voltage for the coil can respectively be regulated independently of the coil currents or of the coil voltages of the other coils. This measure is particularly advantageous to exert both a torque on the rotor by the stator and also a shear force, which can be set as desired, in the radial direction by which the radial position of the rotor—that is its position in the plane perpendicular to the desired axis of rotation—can be actively magnetically regulated. The independent control capability of each coil additionally makes it possible that the position of the rotor with respect to tilts against the desired axis of rotation (two degrees of freedom) can be actively magnetically regulated by the cooperation of the upper stator part and of the lower stator part.

Alternatively, it is a preferred measure if one respective coil is arranged as a winding on each upper stator pole and on each lower stator pole, wherein two respective coils are connected together to an electrical phase, and wherein a respective separate power amplifier is provided for each electrical phase. In this respect, it is possible both to connect two respective coils of the upper poles or two respective coils of the lower poles together and a coil of an upper pole to a coil of a lower pole. In the last-named case, it is preferred for coils respectively arranged above one another to be connected together. The number of the required power amplifiers can be reduced by this connecting together of two coils to an electrical phase. In addition, conventional three-phase controllers can then be used as power amplifiers, for example, in an embodiment having six upper poles and six lower poles in the stator.

It is very particularly preferred with respect to the configuration of the stator for the permanent magnet of each stator to be designed in disk form or ring form, to be magnetized in the axial direction and in each case to connect the upper stator part to the lower stator part. The permanent magnetically generated flux can naturally also be guided through additional magnetically soft parts. The permanent magnet can likewise be made up of a plurality of individual magnets such as segment magnets or block magnets.

Preferred applications comprise the rotary drive being configured as a pumping or mixing apparatus for conveying or mixing fluid substances or as a component of a pumping or mixing apparatus for conveying or mixing fluid substances.

Further advantageous measures and embodiments of the invention result from the dependent claims.

BRIEF DESCRIPTION OF THE DRAWINGS

The invention will be explained in more detail hereinafter with reference to the drawings.

FIG. 12 is as FIG. 4, but for the stator in accordance with FIG. 10;

FIG. 14 is a schematic representation for a variant of the power amplifiers for regulating the coil currents or coil voltages of the stator in accordance with FIG. 10;

FIG. 15 is a perspective view of a third variant for the design of the stator of the first embodiment;

DETAILED DESCRIPTION OF THE EMBODIMENTS

Figure 1:
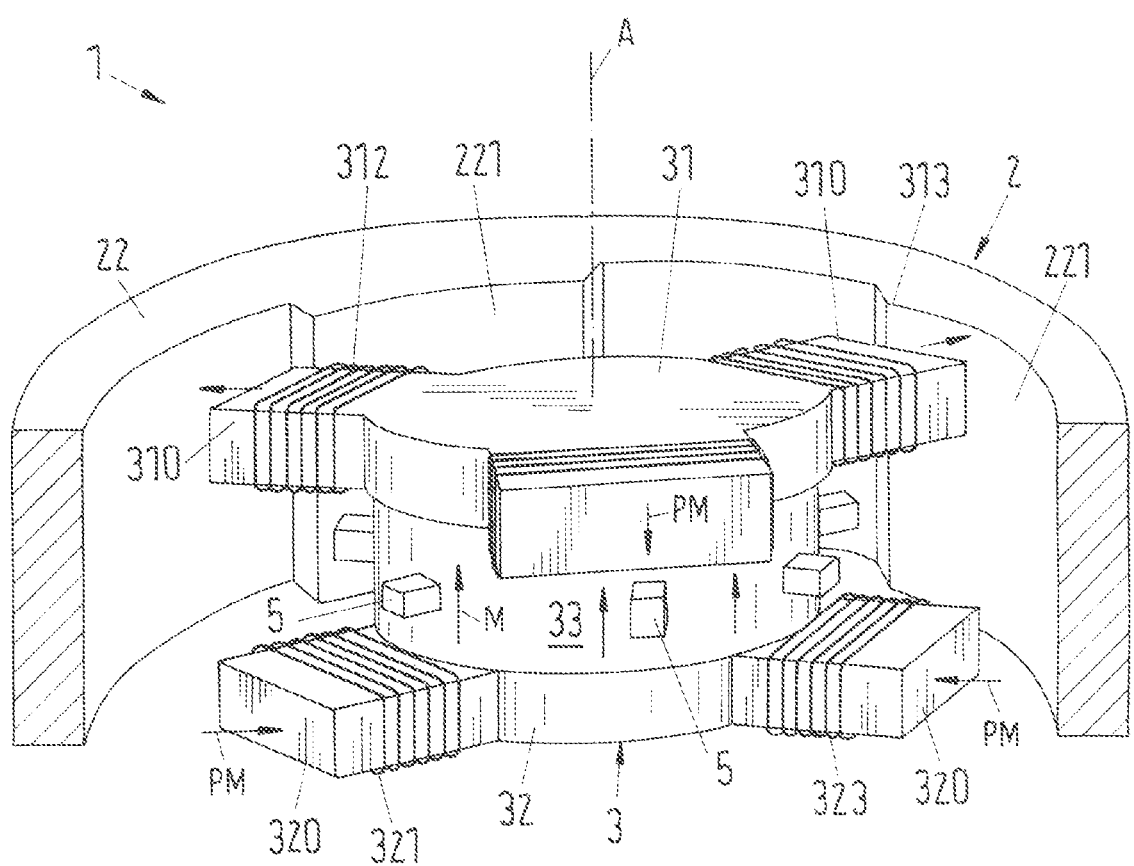
FIG. 1 is a perspective sectional representation of a first embodiment of an electromagnetic rotary drive in accordance with the invention.

FIG. 1 shows in a perspective sectional representation a first embodiment of an electromagnetic rotary drive in accordance with the invention which is designated as a whole by the reference numeral 1. The rotary drive 1 is configured in accordance with the principle of the bearingless motor and comprises a rotor 2 which is magnetically contactlessly drivable and which is free of coils as well as a stator 3 which is configured as a bearing and drive stator by which the rotor 2 can be magnetically contactlessly driven about a desired axis of rotation A in the operating state and can be magnetically contactlessly supported with respect to the stator 3. In the embodiment described here, the stator 3 is arranged inwardly disposed with respect to the rotor 2.

In the following, that axis of rotation is called the desired axis of rotation A about which the rotor 2 rotates when it is in a centered position with respect to the stator 3. The rotor 2 is then centered in a plane which is perpendicular to the center axis of the stator 3 and is not tilted with respect to this plane. The desired axis of rotation A as a rule coincides with the center axis of the stator 3.

In the following, the direction defined by the desired axis of rotation A will be called the axial direction, the directions perpendicular thereto will generally be called the radial direction. That plane perpendicular to the desired axis of rotation A which is the magnetic central plane of the stator 3 is called the radial plane. The radial plane defines the x-y plane of a Cartesian coordinate system whose z axis extends in the axial direction.

The rotor 2 of the rotary drive 1 in accordance with the invention is coil-free, i.e. no windings are provided on the rotor 2. The rotor 2 comprises a magnetically active core 22 which can be surrounded by a plastic jacket in dependence on the configuration. Examples for the configuration of the rotor will be explained further below in connection with FIGS. 22-24. Since it is sufficient for the understanding of the invention, only the magnetically active core 22 of the rotor is shown in most drawing Figures. It is, however, understood that the rotor 2 can naturally comprise other components such as an already mentioned jacket.

Figure 2:
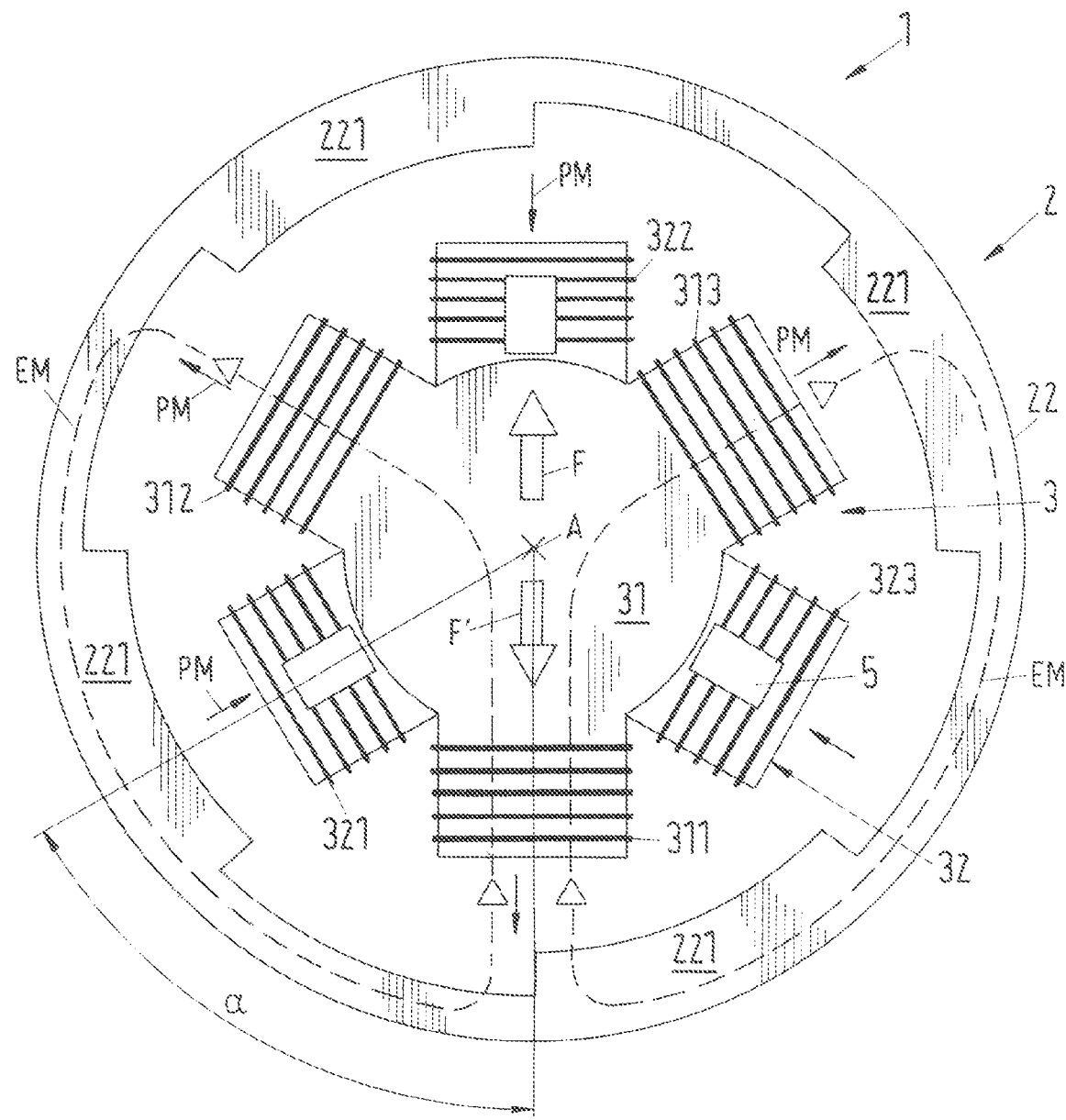
FIG. 2 is a plan view of the stator and of the magnetically active core of the rotor of the first embodiment from the direction of the desired axis of rotation.

For better understanding, FIG. 2 shows a view from the axial direction—that is from the direction of the desired axis of rotation A—toward the stator 3 and toward the magnetically active core 22 of the rotor 2.

In a very especially preferred embodiment of the invention, which is also realized in the embodiment described here, the rotor 2 or the magnetically active core 22 of the rotor 2 does not have any permanent magnets; it is therefore free of permanent magnets. This measure allows a particularly inexpensive embodiment of the rotor 2—for example also as a single-use part—since in particular no rare earths such as neodymium or samarium or compounds or alloys thereof are necessary which are frequently used for the manufacture of permanent magnets for the manufacture of the rotor 2. The dispensing with of these permanent magnets in the rotor also signifies a large advantage under environmental aspects.

Those ferromagnetic or ferrimagnetic materials which are magnetically hard, that is which have a high coercive field strength, are typically called permanent magnets. The coercive field strength is that magnetic field strength which is required to demagnetize a material. Within this application, a permanent magnet is understood as a material which has a coercive field strength, more precisely a coercive field strength of the magnetic polarization, which amounts to more than 10,000 A/m.

If the rotor 2 is therefore free of permanent magnets, this means that the magnetically active core 22 of the rotor only comprises materials whose coercive field strength amounts to at most 10,000 A/m.

The designation that the rotor 2 is "free of permanent magnets" should be understood within the framework of this application that the rotor 2 does not comprise any permanent magnets which make a substantial contribution to the drive field for driving the rotation of the rotor 2. It is naturally possible that other magnets or permanent magnets are provided at the rotor 2 which, for example, only serve for the detection of the angular position of the rotor or which otherwise satisfy a purpose which has nothing to do with the generation of the drive flux for the rotor. The designation "free of permanent magnets" therefore only relates to the drive of the rotor 2.

The magnetically active core 22 of the rotor is preferably produced from a magnetically soft material, for example from iron, nickel iron or silicon iron. In this respect, the magnetically active core 22 can e.g. be manufactured by casting, stamping, pressing of magnetically soft powder with subsequent sintering, forging, shaping or assembling of parts such as metal sheets.

In the first embodiment, the magnetically active core 22 is configured as substantially in a ring shape (see also FIG. 2), wherein a plurality of pronounced rotor poles 221 are provided distributed over the inner periphery of the ring-shaped core 22 which extend radially inwardly. With respect to the axial direction, each rotor pole 221 extends over the total axial height of the ring-shaped magnetically active core 22. In the variant described here, the magnetically active core 22 has four rotor poles 221 which are distributed equidistantly over the inner periphery of the ring-shaped magnetically active core.

The stator 3 is configured as a bearing and drive stator with which the rotor 2c can be driven magnetically contactlessly about the desired axis of rotation A in the operating state—that is it can be set into rotation—and can be supported magnetically contactlessly with respect to the stator 3. The stator 3 and the rotor 2 thus form an electromagnetic rotary drive which simultaneously allows a magnetic support of the rotor 2. This electromagnetic rotary drive 1 is particularly preferably configured according to the principle of the bearingless motor. The bearingless motor has in the meantime become sufficiently well-known to the skilled person so that a detailed description of its function is no longer necessary.

The term bearingless motor means that the rotor 2 is supported completely magnetically, with no separate magnetic bearings being provided. The stator 3 is configured for this purpose as a bearing and drive stator; it is therefore both the stator of the electric drive and the stator of the magnetic support. The stator 3 in this respect comprises 3 windings with which a magnetic rotating field can be generated which, on the one hand, exerts a torque on the rotor 2 which effects its rotation and which, on the other hand, exerts a shear force on the rotor 2 which can be set as desired so that its radial position—that is its position in the radial plane—can be actively controlled or regulated. At least three degrees of freedom of the rotor 2 can thus be actively regulated. The rotor 2 is passively magnetically stabilized, that is cannot be controlled, by reluctance forces with respect to its axial deflection in the direction of the desired axis of rotation A. The rotor 2 can also likewise be stabilized—depending on the embodiment—passively magnetically with respect to the remaining two degrees of freedom, namely tilts with respect to the radial plane perpendicular to the desired axis of rotation A.

An electromagnetic drive and bearing apparatus is known from US-A-2009/121571, for example, in which the stator of the drive and the stator of the magnetic support are combined to form a constructional unit. The stator here comprises a bearing unit, which consists of an upper and a lower bearing plane, and a drive unit, the bearing unit and the drive unit being arranged between said bearing planes. This apparatus therefore also shows a bearing unit which can be separated from the drive unit and which only serves for the magnetic support. Such apparatus are, however, not to be understood as bearingless motors in the sense of the present invention because separate bearing units are actually present here which implement the support of the rotor separately from the drive function. With a bearingless motor in the sense of the present invention, it is not possible to split the stator into a bearing unit and into a drive unit. It is actually this property which gives the bearingless motor its name.

In the bearingless motor, unlike classical magnetic bearings, the magnetic support and the drive of the motor is implemented via electromagnetic rotating fields whose sum produces a drive torque onto the rotor 2, on the one hand, as well as a transverse force which can be set as desired and by which the radial position of the rotor 2 can be regulated. These rotating fields can either be generated separately—that is with different coils—with the support only being able to be implemented by the combination of the rotating fields generated by the two, or the rotating fields can be generated by calculational superposition of the required currents and then with the aid of a single coil system. It is therefore not possible to split the electromagnetic flux generated by the coils of the stator into an electromagnetic flux which only provides the drive of the rotor and into an electromagnetic flux which only implements the magnetic support of the rotor.

The bearingless motor can be configured as an internal rotor, that is with an inwardly disposed rotor and a stator arranged around it, or as an external rotor, that is with an inwardly disposed stator 2 and a rotor 3 arranged around it. In the first embodiment described here, the electromagnetic rotary drive 1 is configured as an external rotor.

In accordance with the invention, the stator 3 comprises an upper stator part 31 having a plurality of pronounced upper poles 310 for carrying upper windings 311, 312, 313 as well as a lower stator part 32 having a plurality of pronounced lower poles 320 for carrying lower windings 321, 322, 323. The upper stator part 31 and the lower stator part 32 are arranged spaced apart from one another with respect to the axial direction. A permanent magnet 33 is provided between the upper stator part 31 and the lower stator part 32.

It is in this respect a substantial aspect, which takes the principle of the bearingless motor into account, that both the upper stator part 31 and the lower stator part 32 each contribute to the drive and to the contactless magnetic support of the rotor.

The axial spacing of the upper stator part 31 from the lower stator part 32 and the thickness of the upper and lower stator parts 31, 32 are preferably dimensioned such that the total axial height of the stator 3 is at least approximately the same height, and preferably is the same height, as the height of the magnetically active core 22 of the rotor 2 in the axial direction.

In the first embodiment described here and shown in FIGS. 1 and 2, the stator 3 comprises exactly three upper poles 310 and exactly three lower poles 320. The upper and lower stator parts 31, 32 are of substantially the same design and are each configured in substantially disk shape, with each pole 310, 320 extending outwardly from the central disk part in the radial direction. The upper and lower stator parts 31, 32 are each produced from a magnetically soft material, for example iron, and can also be configured as a metal sheet stator packet. The upper and lower stators parts 31, 32 are parallel with one another, with the permanent magnet 33 being arranged between them, said permanent magnet being configured in disk shape or in ring shape and connecting the lower stator part 32 to the upper stator part 31. The permanent magnet 33 is magnetized in the axial direction—from the bottom to the top in accordance with the illustration—as the arrows with the reference symbol M indicate. The outer diameter of the permanent magnet 33 is dimensioned such that it is preferably not larger, and is particularly preferably a little smaller, than the diameter of the central disk part of the upper or lower stator part 31, 32. That part of the upper or lower stator part 31, 32 is meant by the central disk part which remains when the poles 310 or 320 are imagined to be not there.

The substantially identical upper and lower stator parts 31 and 32 are arranged rotated relative to one another by an angle $\alpha$ with respect to the desired axis of rotation A in the variant of the first embodiment shown in FIG. 1 and FIG. 2 (see FIG. 2) so that the upper poles 310, viewed in the axial direction, are each arranged in a gap between two adjacent lower poles 320. In the embodiment shown in FIGS. 1 and 2, the angle $\alpha$ amounts to 60° so that each upper pole 310 is arranged, viewed in the axial direction, exactly centrally between a respective two adjacent poles 320 of the lower stator part 32. Such a particularly symmetrical design can also be achieved for other numbers of stator poles 310, 320. If N designates the total number of all upper and lower poles 310, 320, the angle $\alpha$ for this symmetrical arrangement is determined according to the relationship $\alpha=360°/N$.

This rotated arrangement of the upper stator part 31 relative to the lower stator part 32 in particular has the advantage that, with a smaller number of upper and lower poles 310, 320, for example with three or four respective lower and upper poles 310, 320, a force effect on the rotor 2 can be generated with one of the two stator parts 31 or 32 by the interplay of the two stator parts 31, 32 for each relative angular position of the rotor 2 toward the stator 3, whereas a torque can be generated on the rotor 2 with the other of the two stator parts 32 or 31 as will be explained further below.

A respective coil 321, 322, 323, 311, 312, 313 is provided as a winding on each of the lower and upper poles 320, 310 with which coils an electromagnetic rotating field can be generated which exerts a torque on the rotor 2. At the same time, a shear force which can be set as desired can be exerted on the rotor 2 by the coils 321, 322, 323, 311, 312, 313 according to the principle of the bearingless motor, by which shear force the position of the rotor 2 can be actively magnetically regulated in the radial plane.

Position sensors 5 are furthermore provided with which the radial position of the rotor 2—that is its position in the radial or x-y plane—can be determined. The position sensors 5 are preferably configured as Hall sensors or eddy current sensors and are in signal connection with a control and regulation device, not shown, via signal lines not shown in any more detail.

It is a customary and known measure to provide a total of four position sensors 5 to determine the position of the rotor 2. In this respect, the position sensors 5 are disposed diametrically opposite pair-wise. In principle, two position sensors 5 are sufficient to determine the position of the rotor 2 in the x-y plane, namely one per coordinate direction. It is, however, preferred to provide four position sensors 5 in order thus to allow a more accurate determination of the position of the rotor 2 from the difference signal of the position sensors 5 oppositely disposed pair-wise.

Such an arrangement of the position sensors 5 is naturally also possible with the rotary drive in accordance with the invention. A variant is shown in FIG. 1 in which a different arrangement of the position sensors 5 is provided. In this variant, the position sensors 5 are arranged in the stator 3, approximately at the center between the upper and lower stator parts 31, 32, and preferably distributed equidistantly over the outer periphery of the permanent magnet 33. In this arrangement, at least five position sensors 5 are required, with an embodiment having six or eight position sensors 5 being preferred. Both the radial position of the rotor 2 and the angle of rotation of the rotor 2 can be determined by this arrangement of the position sensors 5 using the sensor signals. The position sensors 5 can, for example, respectively be eddy current sensors, optical sensors, capacitive sensors or magnetic field sensors such as Hall sensors or GRM sensors. With magnetic field sensors, a small permanent magnet is preferably arranged behind the sensor if the scatter field of the permanent magnet 33 should not be sufficient.

For a better understanding, the extent of the permanent magnetic flux generated by the permanent magnet 33 is indicated schematically by the arrows provided with the reference symbol PM in FIGS. 1 and 2. The permanent magnet flux extends in the axial direction in accordance with the illustration (FIG. 1) upwardly through the permanent magnet 33, is then guided radially outwardly in the upper stator part 31 through the upper poles 310 into the magnetically active core 22 of the rotor 2, extends there in the axial direction in accordance with the illustration downwardly and is conducted at the lower axial end of the magnetically active core 22 radially inwardly into the lower poles 320 of the lower stator part 32 from where it is guided in the axial direction back into the permanent magnet.

The generation of a radially outwardly active shear force F' on the rotor 2 is illustrated with exemplary character for a rotary position of the rotor 2 relative to the stator 3 in FIG. 2. F designates the opposing force of equal amount which acts on the stator 3. For this purpose, beside the permanent magnetic flux which is indicated by the arrows having the reference symbol PM, the electromagnetic flux generated by the coils 311, 312, 313 arranged on the upper poles 310 is also indicated by the lines with the reference symbols EM shown as chain-dotted lines.

As can be recognized, the permanent magnetic flux PM does not generate any resulting force on the rotor 2 due to the symmetrical force introduction. The electromagnetic flux EM generated using the coils 311, 312, 313 in this snapshot exits the stator 3 radially outwardly at the coils 312 and 313 and enters into the respective oppositely disposed rotor poles 221 in the rotor 2. The total electromagnetic flux EM then exits the rotor pole 221 at the coil 311 and is guided radially inwardly into the upper pole 310 which carries the coil 311. In sum, the radially outwardly acting shear force F thereby results on the stator 3 which is indicated by the arrow having the reference symbol F in FIG. 2 and a shear force acting in the opposite direction on the rotor 2. It can be recognized with reference to this example how a shear force, which can be set as desired, can be generated on the rotor 2 by the stator 3, with which shear force the radial position of the rotor 2—that is its position in the radial plane—can be actively magnetically regulated. It can likewise be seen that the electromagnetic flux EM is always led, in addition to the region of the air gaps between the rotor 2 and the stator 3, through magnetically soft material and not through the permanent magnet 33.

For the control of the coils 311, 312, 313, 321, 322, 323 for generating the electromagnetic rotating field, a setting device, not shown, is present which comprises an amplifier unit 8 (see FIG. 3, FIG. 4) and is controlled by the control and regulation device (not shown). There are a plurality of variants for the embodiment of the amplifier unit 8 of which two will be described in the following which are suitable for the first embodiment with the total of six coils 311, 312, 313, 321, 322, 323. It is advantageous in this respect if a respective separate power amplifier 81 is provided for each of the coils 311, 312, 313, 321, 322, 323, with which power amplifier the coil current or the coil voltage for this coil can be regulated independently of the coil currents or the coil voltages of the other coils.

In the following, reference will be made with exemplary character to the case that the respective coil current is regulated as a variable.

In the embodiment described here, reference is made to the case that each of the coils 311, 312, 313, 321, 322, 323 is respectively configured as exactly one discrete coil which per se forms an electrical phase. Such embodiments are naturally also possible in which some or each of the coils 311, 312, 313, 321, 322, 323 respectively comprise more than one discrete coil.

Since therefore six coils 311, 312, 313, 321, 322, 323 are provided in the embodiment described here which each belong to a separate electrical phase, a total of six power amplifiers 81 have to be provided in the amplifier unit 8.

Figure 3:
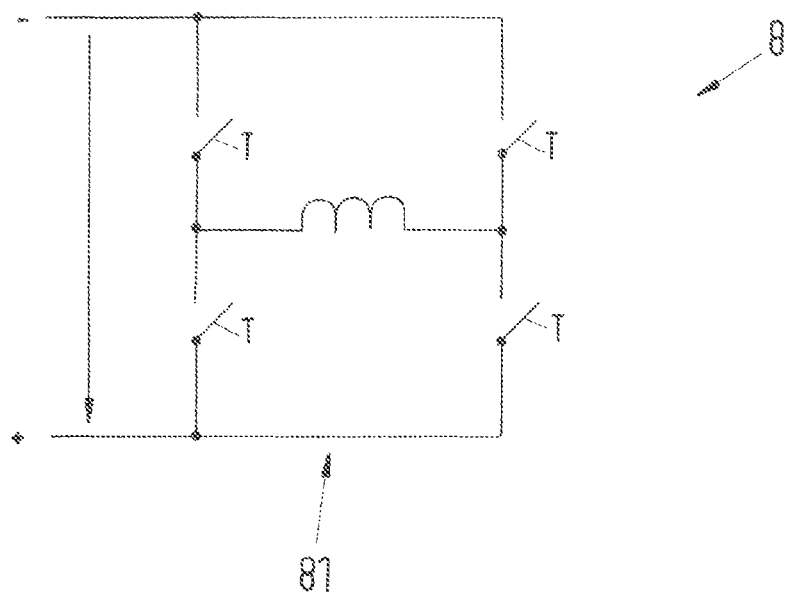
FIG. 3 is a schematic representation of an embodiment of a power amplifier for regulating the coil current or the coil voltage.

In the variant shown in FIG. 3, the amplifier unit 8 comprises a total of six power amplifiers 81, namely one for each electrical phase. Each power amplifier 81 is a bipolar power amplifier 81 which is respectively configured as an H bridge circuit in a manner known per se. Only one of these H bridge circuits is shown in FIG. 3 because the circuit diagrams of the other five have an identical appearance.

The name "bipolar power amplifier" means that both the phase currents and the phase voltages can each adopt a positive and a negative sign.

The H bridge circuits (see FIG. 3) are implemented in a manner known per se with switching transistors T and flyback diodes, not shown, and are operated at the operating potentials + and −. The operation potential—is the ground potential, for example.

Figure 4:
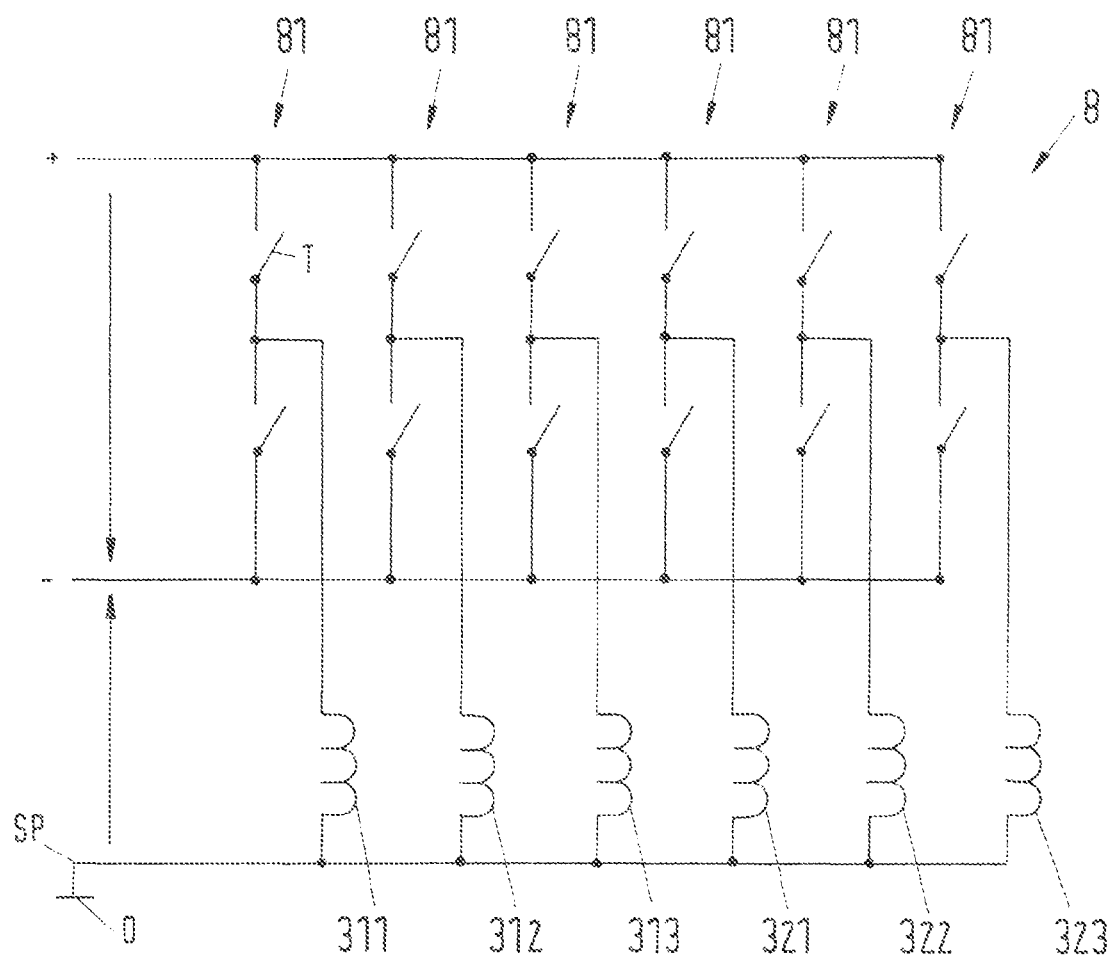
FIG. 4 is a schematic representation of a variant of the power amplifiers for regulating the six coil currents or coil voltages of the first embodiment.

FIG. 4 shows another variant for the power amplifier 81 of the amplifier unit 8 for the separate regulation of the coil currents (or coil voltages) in the coils 311, 312, 313, 321, 322, 323. In this variant, each of the six power amplifiers 81 is a respective bridge branch of the amplifier unit 8. A respective one bridge branch of the amplifier unit 8 is provided as a separate bipolar power amplifier 81 for each of the coils 311, 312, 313, 321, 322, 323 or for each of the separate electrical phases. Each bridge branch can supply one of the coils 311, 312, 313, 321, 322, 323 with the respective coil current or the respective coil voltage in a manner known per se by switching transistors T and flyback diodes (not shown). The amplifier unit 8 is operated at two operating potentials which are marked by + and − in FIG. 4. These operating potentials +, − are DC voltage potentials. The midpoint potential O, which is the ground potential, for example, lies between these two operating potentials. Each coil 311, 312, 313, 321, 322, 323 is connected on the one hand to the bipolar power amplifier 81 supplying it. On the other hand, each coil 311, 312, 313, 321, 322, 323 is connected to a common neutral point SP which lies on the midpoint potential O. The neutral point SP is preferably, but not necessarily, configured as a loadable neutral point SP, that is it is connected to a loadable potential so that, apart from the six coil currents, an additional current can flow off over the neutral point SP or can flow into it. This means that the usual neutral point condition that the sum of the coil currents at the neutral point SP always has to be zero is no longer necessary with this circuit. This has the consequence that each coil current can be regulated completely independently of the other coil currents.

Figure 5:
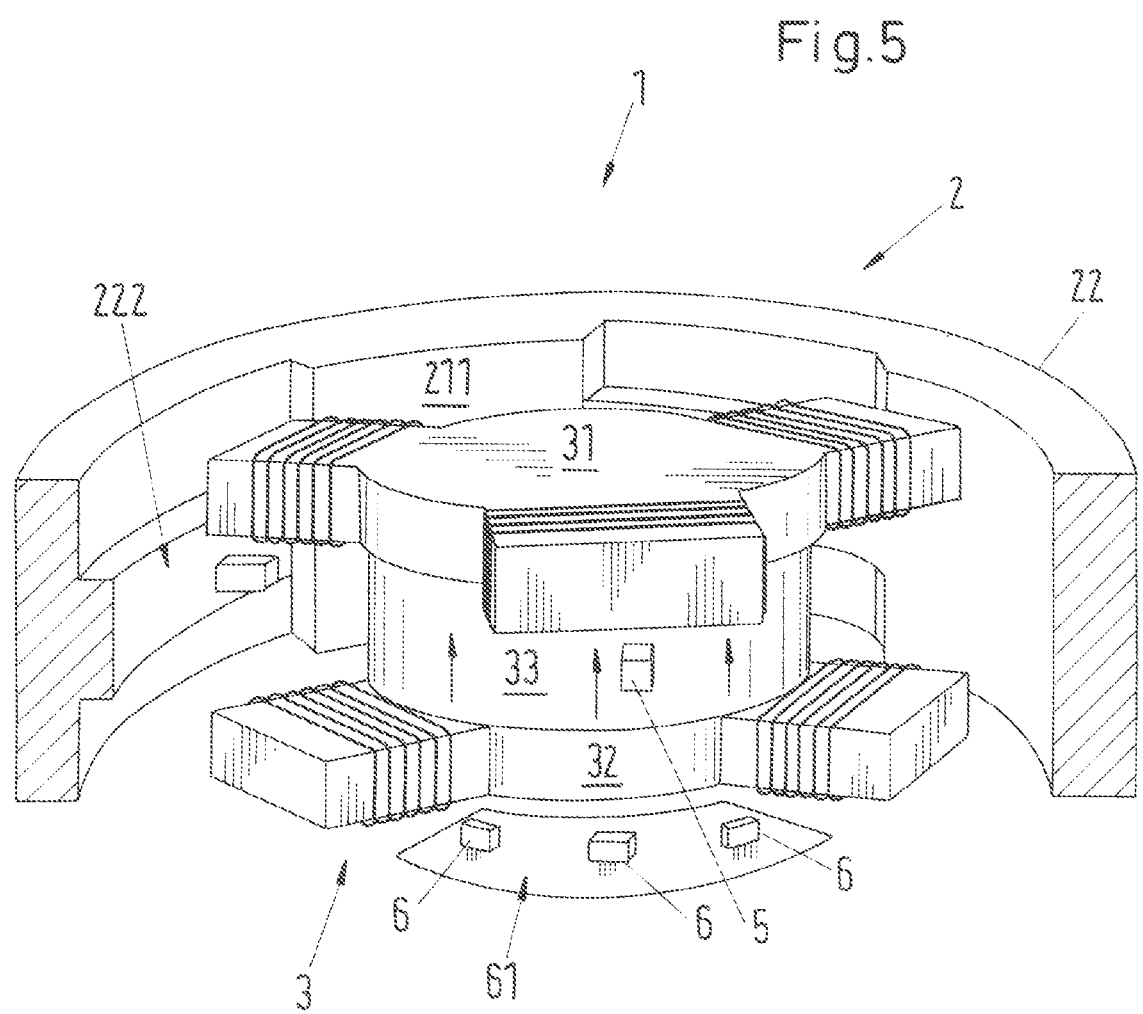
FIG. 5 is a perspective sectional representation of a first variant of the first embodiment with an alternative design of the magnetically active core of the rotor.

FIG. 5 shows in a perspective sectional representation of the stator 3 and of the magnetically active core 22 of the rotor 2 a first variant of the first embodiment with an alternative design of the magnetically active core 22 of the rotor 2. In this variant of the magnetically active core 22 of the rotor 2, it is also configured in substantially ring shape, wherein a peripheral ring 222 is provided at the center, however, (with respect to the axial direction) which has an inner diameter constant over the total periphery. The rotor poles 221—four here—are then provided above and beneath the rings 222 as already described.

This embodiment makes it possible to reduce the number of position sensors 5 in comparison with the variant shown in FIG. 1. It is possible in principle to manage with only two position sensors 5 in the embodiment with the cylindrical peripheral ring 222, namely one for each of the two Cartesian coordinate axes of the radial plane. To increase the accuracy of the position determination, however, it is also preferred here to provide a total of four position sensors 5 of which a respective two are arranged diametrically opposite one another pair-wise and then to use the respective difference signal of these two oppositely disposed position sensors 5 to determine the rotor position.

FIG. 5 furthermore shows three further sensors 6 which are used for the determination of the respective current rotary position of the rotor 2. The current angle of rotation (measured against any desired determinable zero angle) of the rotor 2 relative to the stator 3 can be determined with them. This angle of rotation is as a rule required for the regulation of the electromagnetic rotary drive 1 in an embodiment in accordance with the principle of the bearingless motor. The three sensors 6 are, for example, arranged on an electronic print 61 arranged beneath the stator in accordance with the illustration. All three sensors 6 are arranged, viewed in the axial direction, in the same gap between two adjacent lower poles 320 of the lower stator part 32 and all have the same spacing from the desired axis of rotation A. The sensors 6 are preferably configured as Hall sensors or as eddy current sensors, with Hall sensors being preferred, for example, on the presence of a metallic separating can between the rotor 2 and the stator 3. Depending on the configuration, the magnetic scatter field at the location of the sensors 6 is sufficient to determine the respective current value of the angle of rotation of the rotor 2. If this scatter field is not sufficient, each of the Hall sensors 6 can respectively be equipped with a small permanent magnet (not shown) which is, for example, adhesively bonded to the respective sensor 6.

It is understood that the arrangement described here for the determination of the current angle of rotation of the rotor 2 with the sensors 6 can also be implemented in the same manner or in analogously the same manner in all other variants and in all other embodiments.

Figure 6:
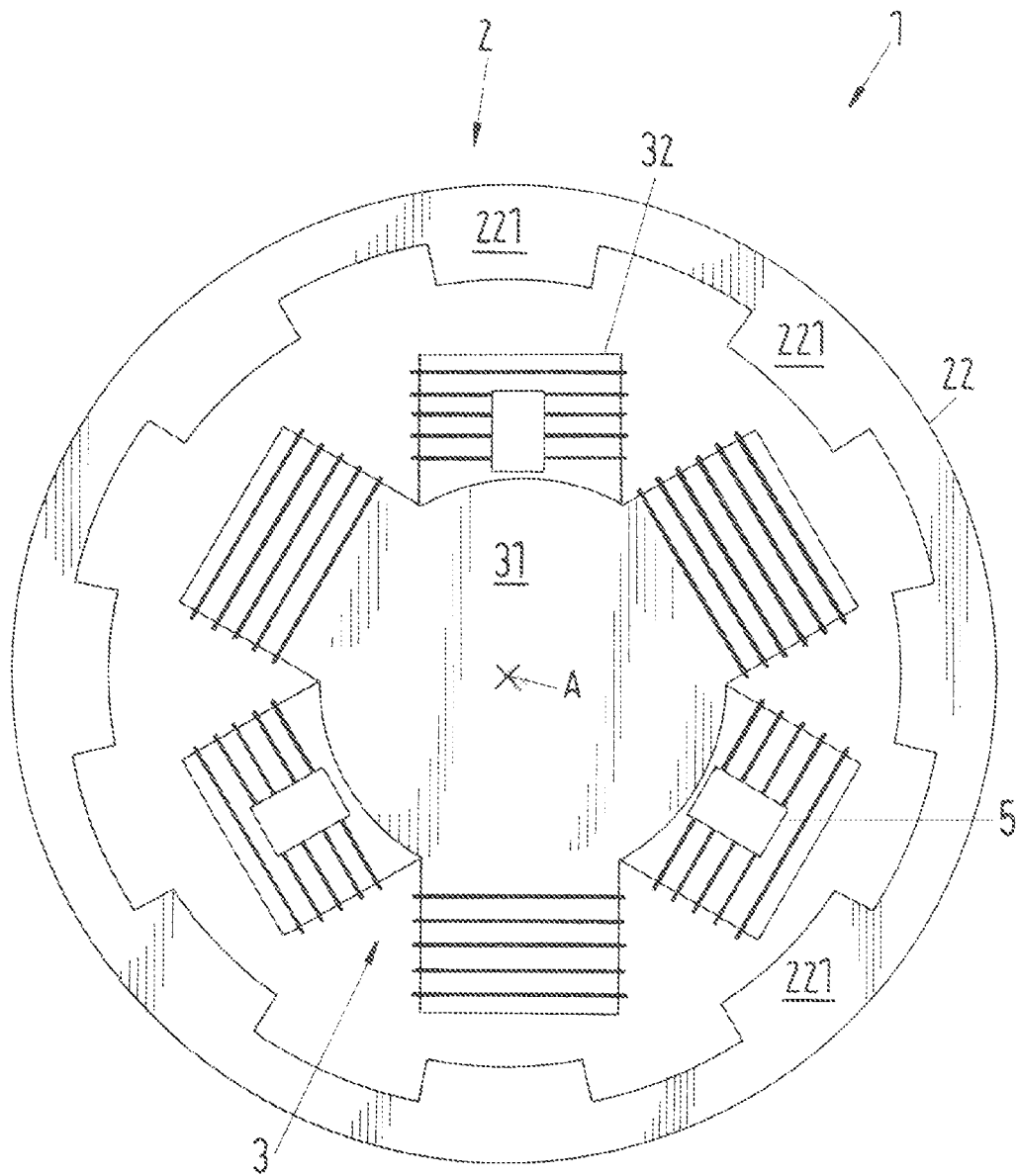
FIG. 6 is a plan view of the stator and of the magnetically active core of the rotor from the direction of the desired axis of rotation for a second variant of the first embodiment with an alternative design of the magnetically active core of the rotor.

FIG. 6 shows a plan view of the stator 3 and of the magnetically active core 22 of the rotor 2 from the direction of the desired axis of rotation A for a second variant of the first embodiment with an alternative design of the magnetically active core 22 of the rotor 2. In this variant, the magnetically active core 22 of the rotor 2 has a total of eight rotor poles 221 which are distributed equidistantly over the inner periphery of the magnetically active core 22 of the rotor 2 and which all have the same length measured in the peripheral direction. The magnetically active core 22 of the rotor can also have the peripheral ring 222 shown in FIG. 5 in this variant.

The increase in the number of rotor poles 221 to a number which does not correspond to a multiple of the number of poles 310 or 320 of the stator 3 has the advantage that the number of possible positions of engagement in which no resulting torque can be exerted by the stator 3 on the rotor 2 can in particular be considerably reduced or even brought to zero in those embodiments of the electromagnetic rotary drive 1 which have a single-phase characteristic. The problem of the positions of engagement or latch positions (or latch torques) is in particular known from the technology of single-phase motors. There are certain relative angular positions between the stator 3 and the rotor 2 in which no resulting torque can be effected on the rotor 2 by the stator 3. If such an angular position coincides with a latch position, that is a position in which the zero latch torque is at a maximum, the motor can no longer start up independently.

Figure 7:
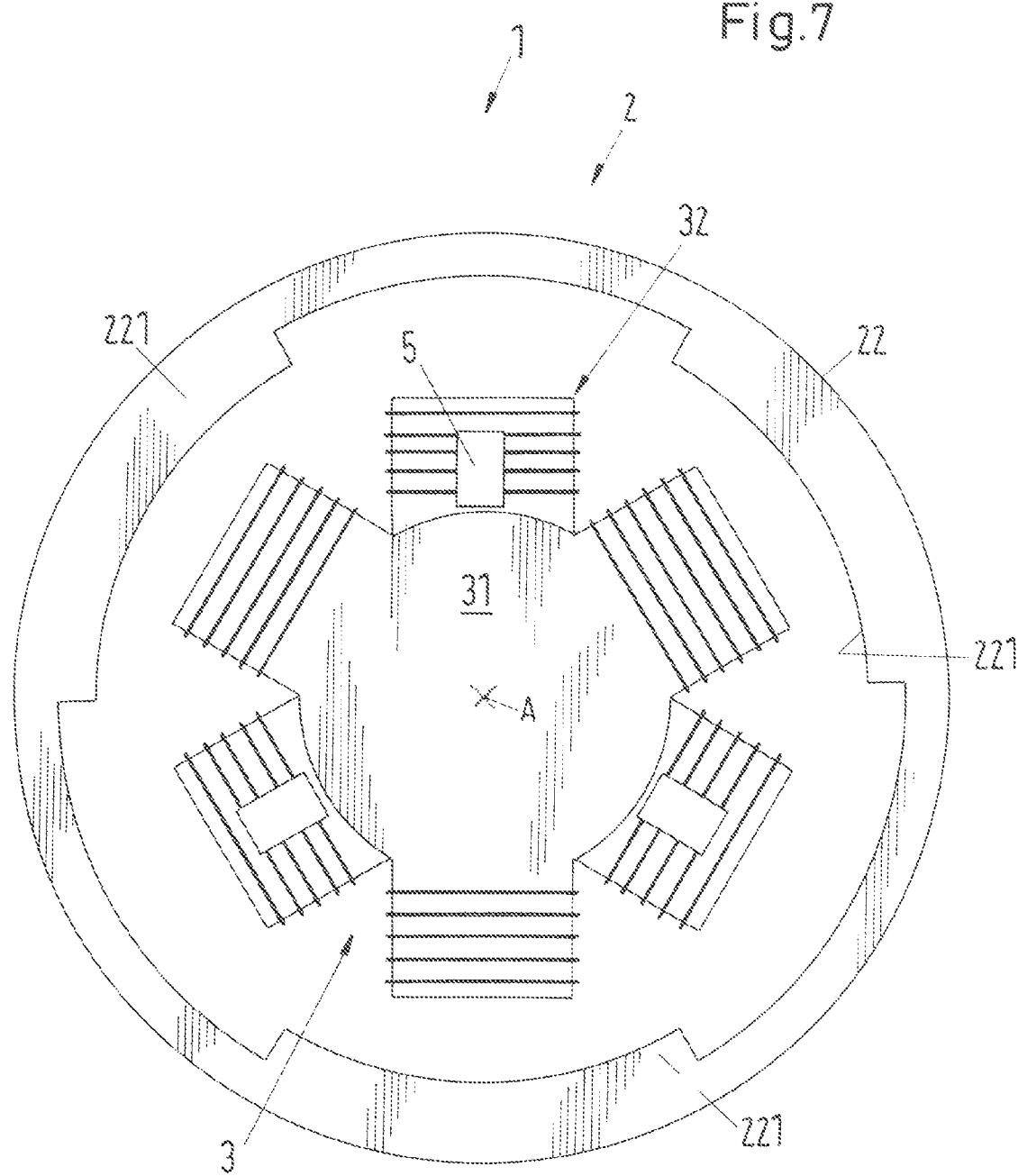
FIG. 7 is a plan view of the stator and of the magnetically active core of the core from the direction of the desired axis of rotation for a third variant of the first embodiment with an alternative design of the magnetically active core of the rotor.

FIG. 7 shows in a representation analog to FIG. 6 a plan view of the stator 3 and of the magnetically active core 22 of the rotor 2 from the direction of the desired axis of rotation A for a third variant of the first embodiment with an alternative design of the magnetically active core 22 of the rotor 2. In this variant, the magnetically active core 22 of the rotor 2 has a total of three rotor poles 221 which are distributed equidistantly over the inner periphery of the magnetically active core 22 of the rotor 2 and which all have the same length measured in the peripheral direction. The magnetically active core 22 of the rotor can also have the peripheral ring 222 shown in FIG. 5 in this variant. In embodiments in which the number of the rotor poles 221 coincides with the number of the upper poles 310 or lower poles 320 of the stator 3 or corresponds to a multiple of the number of these poles 310 or 320, magnetic radial forces can be generated in any angular position of the rotor 2. On the other hand, such embodiments are unfavorable with respect to torque formation if the rotary drive has single-phase characteristics since the positions of engagement of the rotor 2 coincide exactly with the angular positions in which no torque can be produced.

To be able to generate a start-up moment in the positions of engagement of the rotor, it is advantageous in this respect for the rotor poles 221 to be configured or arranged at least slightly asymmetrically. There are a number of possibilities of achieving this asymmetry of which only some are mentioned by way of example here. It is thus possible, for example, not to distribute the rotor poles 221 exactly equidistantly over the periphery of the magnetically active core 22, or the lateral boundary edges of the rotor poles 221 can be configured asymmetrically, for example with different chamfers. It is also possible that the individual rotor poles 221 have at least slightly different lengths—measured in the peripheral direction. The extent of a rotor pole 221 can furthermore extend over its length viewed in the peripheral direction in the radial direction.

Figure 8:
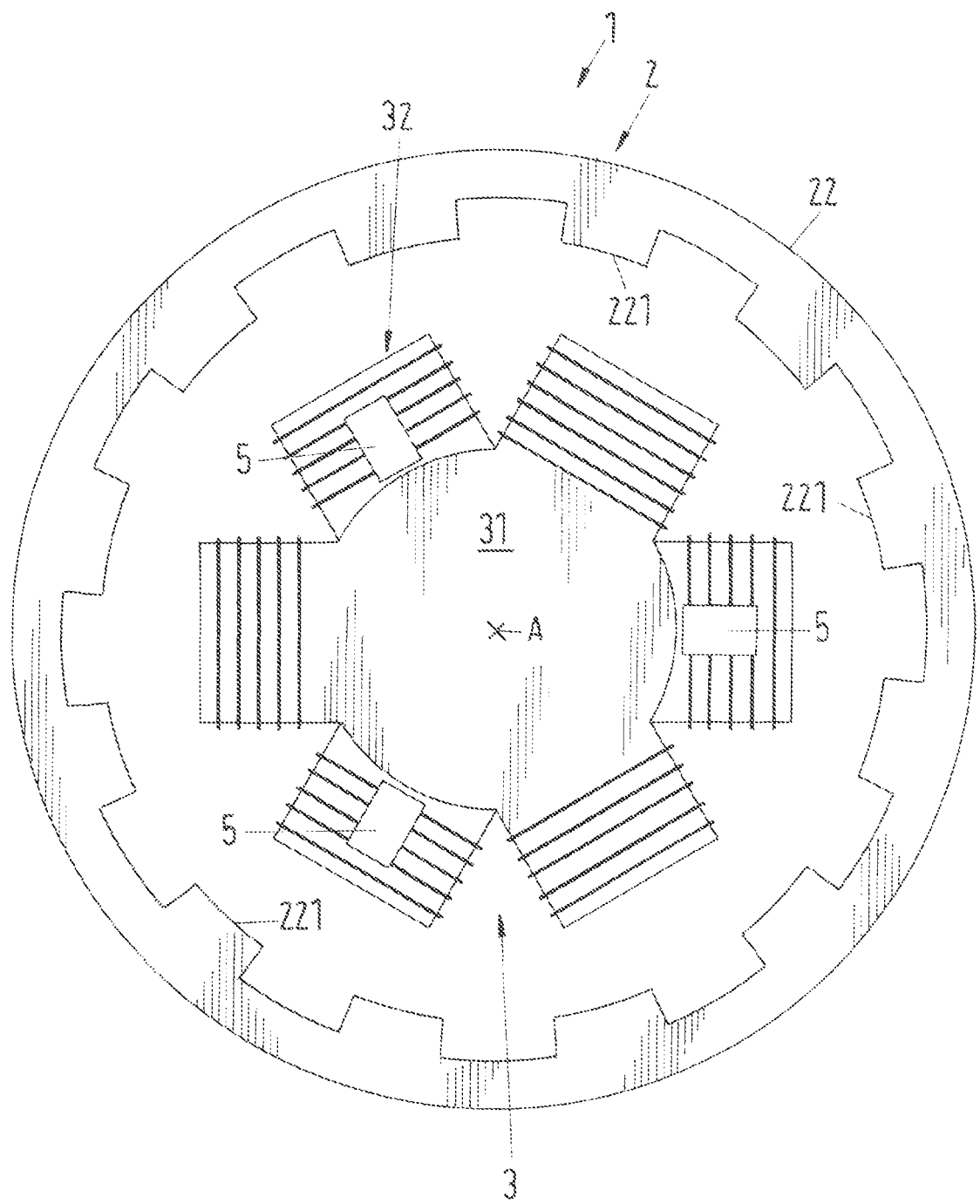
FIG. 8 is a plan view of the stator and of the magnetically active core of the rotor from the direction of the desired axis of rotation for a fourth variant of the first embodiment with an alternative design of the magnetically active core of the rotor.

FIG. 8 shows in a representation analog to FIG. 6 a plan view of the stator 3 and of the magnetically active core 22 of the rotor 2 from the direction of the desired axis of rotation A for a fourth variant of the first embodiment with an alternative design of the magnetically active core 22 of the rotor 2. In this variant, the magnetically active core 22 of the rotor 2 has a total of twelve rotor poles 221 which are distributed equidistantly over the inner periphery of the magnetically active core 22 of the rotor 2 and which all have the same length measured in the peripheral direction. The magnetically active core 22 of the rotor can also have the peripheral ring 222 shown in FIG. 5 in this variant.

The comparatively high number of twelve rotor poles 221 is in particular advantageous with respect to the radial force regulation since the influence of the rotor angle on the radial force amplitude decreases as the pole number increases. The symmetry of the arrangement is additionally of advantage with respect to the radial force regulation. Since the number of rotor poles 221, however, corresponds to a multiple of the number of the upper poles 310 and lower poles 320 of the stator 3 and since the rotary drive in accordance with the embodiment in FIG. 8 has single-phase characteristics, the positions of engagement also coincide with rotor angles here at which no torque can be achieved. Additional measures are also provided here so that the rotary drive 1 can start up. In addition to the measures already discussed in connection with FIG. 7, the measured described in the following with reference to FIG. 9 can also be used in the embodiment of FIG. 8.

Figure 9:
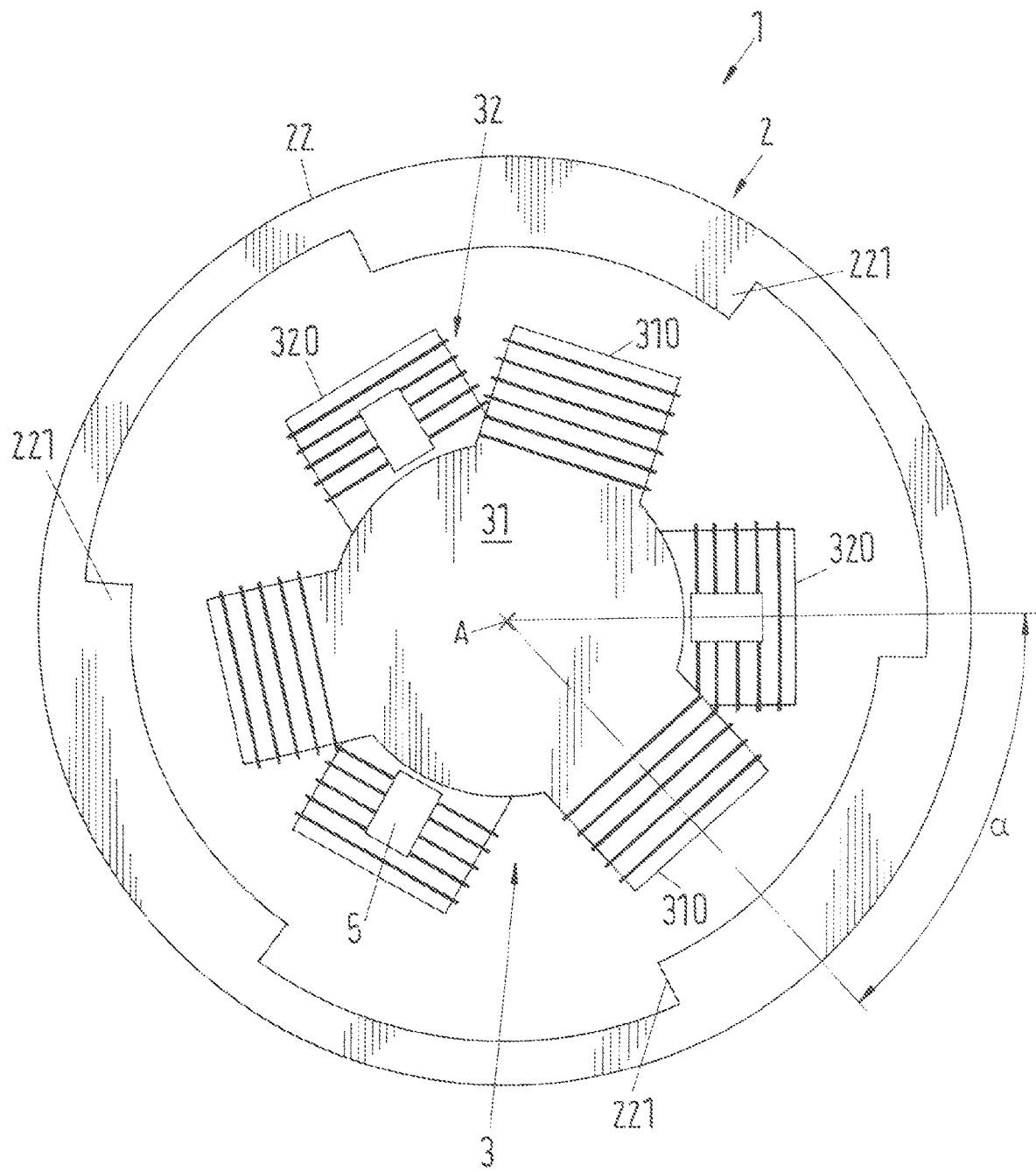
FIG. 9 is a plan view of the stator and of the magnetically active core of the rotor from the direction of the desired axis of rotation for a first variation of the first embodiment with an alternative design of the stator.

FIG. 9 shows a plan view of the stator 3 and of the magnetically active core 22 of the rotor 2 from the direction of the desired axis of rotation A for a first variant of the first embodiment with an alternative design of the stator 3. In this variant, the substantially identical upper and lower stator parts 31 and 32 are also arranged rotated by an angle α relative to one another with respect to the desired axis of rotation A so that the upper poles 310 are arranged, viewed in the axial direction, in each case between two adjacent lower poles 320. The angle α in the embodiment shown in FIG. 9, however, does not satisfy the condition α=360°/N, where N is the total number of all upper and lower poles 310, 320 (here therefore N=6) so that the upper poles 310 no longer lie exactly centrally between two adjacent lower poles 320. This has the consequence that, viewed in the axial direction, the upper poles 310 are admittedly still arranged in gaps between two adjacent lower poles 320, but the upper poles 310 and the lower poles 320 overlap a little, viewed in the axial direction. The angle α amounts to 45°, for example, in FIG. 9.

This is also an advantageous measure to ensure a starting up from positions of engagement, in particular when the rotary drive 1 has a single-phase characteristic such as in the embodiment in accordance with FIG. 9.

Figure 10:
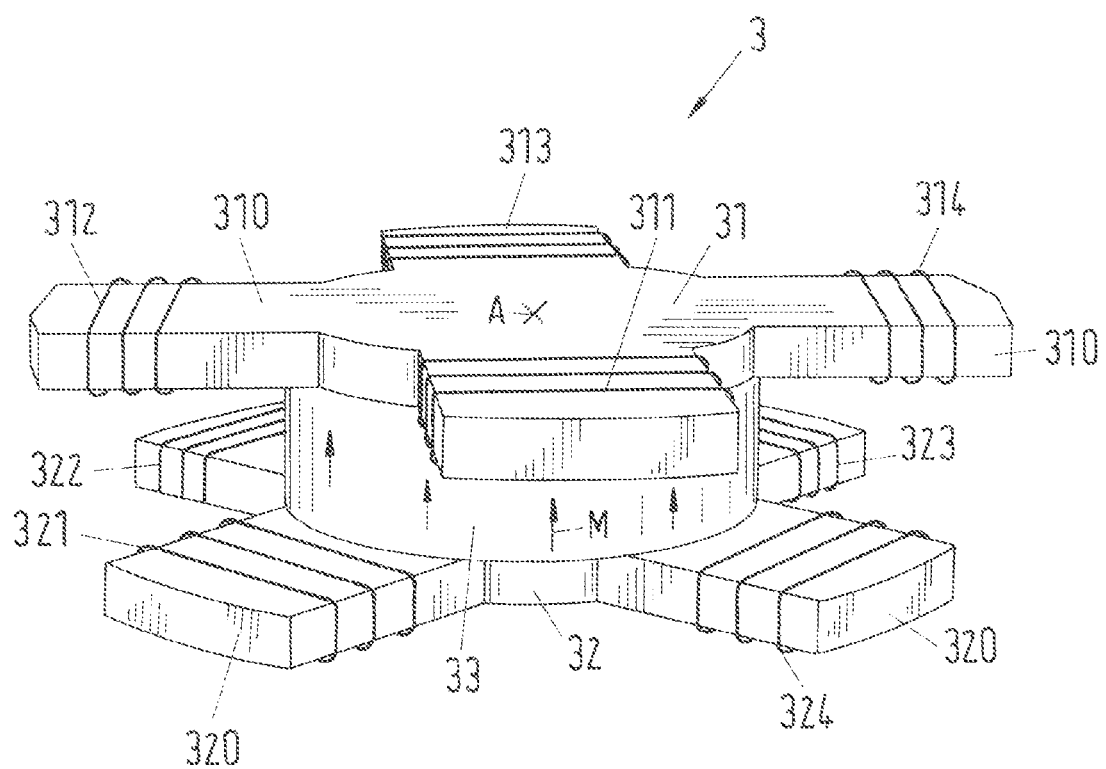
FIG. 10 is a perspective view of a second variant for the design of the stator of the first embodiment.

FIG. 10 shows in a perspective view a second variant for the configuration of the stator 3 of the first embodiment. In this variant, the upper stator part 31 has exactly four upper poles 310 of which each carries an upper coil 311, 312, 313, 314 as a winding. The lower stator part 32 has exactly four lower poles 320 of which each caries a lower coil 321, 322, 323, 324 as a winding. In this variant, the number of the upper poles 310 is also equal to the number of the lower poles 320, wherein here, however, the number of the upper poles 310 and the number of the lower poles 320 is respectively an even number, namely four. Both the upper poles 310 and the lower poles 320 are each arranged equidistantly with respect to the peripheral direction, that is the angle between adjacent poles 310, 320 amounts in each case to 90° both in the upper stator part 31 and in the lower stator part 32.

The substantially identically configured upper and lower stator parts 31 and 32 are arranged rotated relative to one another by an angle α=45° with respect to the desired axis of rotation A in the variant shown in FIG. 10 so that the upper poles 310, viewed in the axial direction, are each arranged in a gap between two adjacent lower poles 320. Since here the relationship α=360°/N is satisfied with N=8, each upper pole 310 is arranged, viewed in the axial direction, exactly centrally between two respective adjacent poles 320 of the lower stator part 32.

Figure 11:
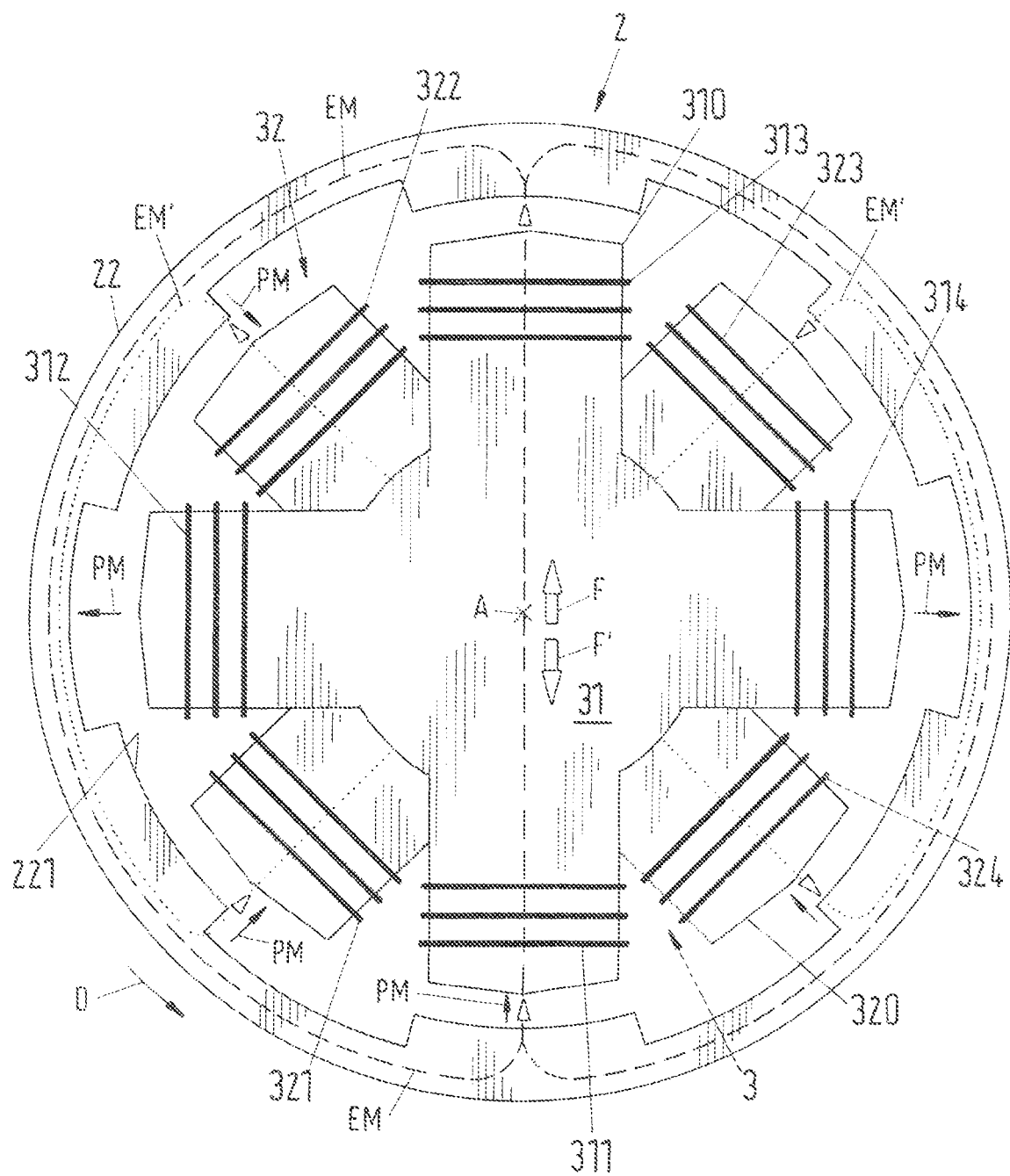
FIG. 11 is a plan view of the stator of FIG. 10 together with the magnetically active core of the rotor.

FIG. 11 shows a plan view of the stator 3 from FIG. 10 together with the magnetically active core 22 of the rotor 2 which has six rotor poles 221 here. The interplay of the two stator parts 31, 32 for the generation of force and torque on the rotor 2 will be explained with reference to FIG. 11. Since the permanent magnetic flux can be left out of consideration for this purpose, only the electromagnetic flux will be looked at in the following. FIG. 11 shows a snapshot of the rotary position of the magnetically active core 22 of the rotor 2 relative to the stator 3. The extent of the electromagnetic flux on the plane of the lower stator part 32 is indicated by the dotted lines having the reference symbol EM'; the extent of the electromagnetic flux on the plane of the upper stator part is indicated by the dashed line having the reference symbol EM. As can be recognized by the extent of the electromagnetic flux EM on the plane of the upper stator part 31, the upper stator part 31 generates a resulting force on the stator 3 which is indicated by the arrow F and which is directed radially outwardly as a shear force and an oppositely disposed force F' of equal amount is corresponding directed to the rotor 2. However, no resulting torque is exerted on the rotor on this plane. It can equally be recognized that the electromagnetic flux EM' does not exert any resulting force on the rotor 2 on the plane of the lower stator part 32, but a resulting torque is exerted on the rotor 2 which is indicated by the arrow D. In this snapshot, the upper stator part therefore generates the shear force F on the rotor 2, while the lower stator part 32 generates the torque D.

If the rotor 2 has rotated onward by 45°, the situation reverses; the lower stator part 32 then generates the force on the rotor and the upper stator part 31 effects the resulting torque.

The setting device for controlling the stator 3 also comprises an amplifier unit 8 in the variant shown in FIG. 10 and FIG. 11, said amplifier unit having a separate power amplifier 81 for each of the eight coils 311, 312, 313, 314, 321, 322, 323, 324 and the coil current for each of the coils can be regulated by said power amplifier independently of the coil currents of the respective other coils.

As already explained in connection with FIG. 3, it is also possible here that each separate power amplifier is respectively configured as an H bridge circuit in accordance with FIG. 3, wherein eight H bridges are naturally then provided as power amplifiers 81 for the variant described here.

Alternatively, each power amplifier 81 can here also be configured as a respective bridge branch of an amplifier unit 8, in analogously the same manner as has been described in connection with FIG. 4. The corresponding circuit is shown in FIG. 12. The neutral point SP is here also preferably, but not necessarily, configured as a loadable neutral point.

In the variant shown in FIG. 10 or FIG. 11, it is also possible to connect two respective coils together to an electrical phase, whereby the number of required power amplifiers reduces because a separate power amplifier 81 is only required for each electrical phase.

The respective oppositely disposed coils are preferably connected together pairwise in each case in the upper stator part 31 and in the lower stator part 32. Due to the symmetry, the coil currents in the two coils forming a pair are then of equal and opposite amounts.

The following coil pairs are therefore each connected together to form an electrical phase: In the lower stator part 32, the coil 321 is connected together with the coil 323 and the coil 322 with the coil 324. In the upper stator part 31, the coil 311 is connected together with the coil 313 and the coil 312 with the coil 314.

Figure 13A:
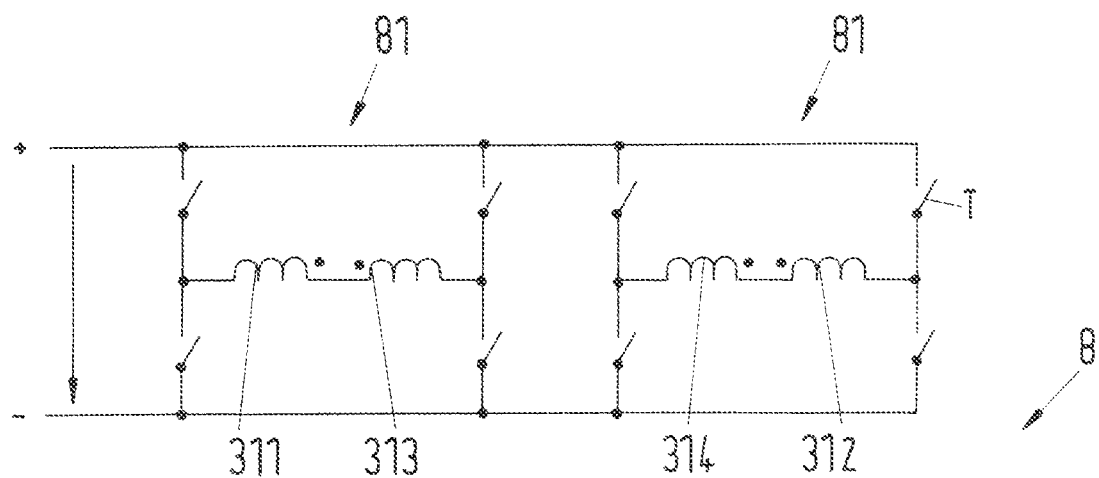
FIG. 13A and FIG. 13B are schematic representations for a variant of the power amplifiers for regulating the coil currents or coil voltages of the stator in accordance with FIG. 10.
Figure 13B:
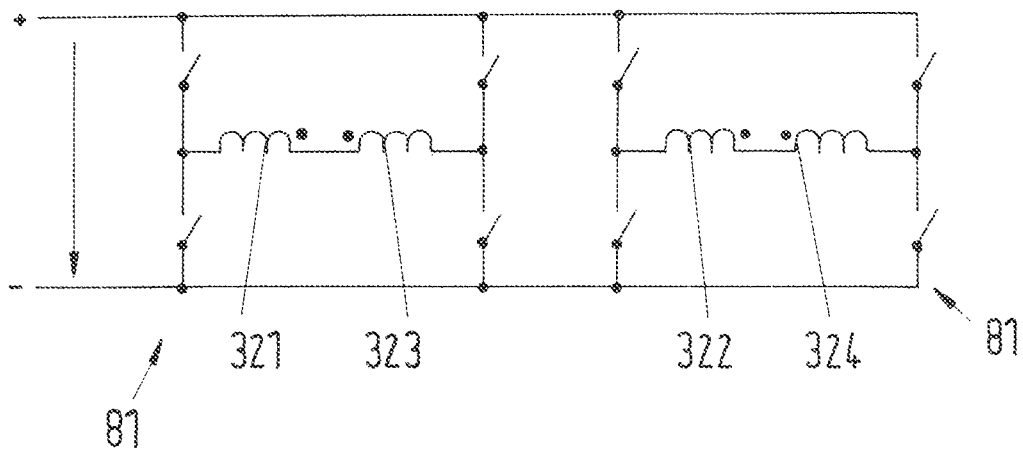

The corresponding circuit diagram with the separate power amplifiers 81 for each electrical phase is shown in FIG. 13A and FIG. 13B for the variant with H bridge circuits for the separate power amplifiers 81 and in FIG. 14 for the variant with bridge branches. In the circuit shown in FIG. 14, however, it is now necessary that the neutral point SP is loadable.

FIG. 15 shows in a perspective view a third variant for the configuration of the stator 3 of the first embodiment. For a better understanding, FIG. 16 shows a plan view from an axial direction of the stator 3 of FIG. 15 together with the magnetically active core 22 of the rotor 2.

In this variant, the upper stator part 31 has exactly six upper poles 310 of which each carries an upper coil 311, 312, 313, 314, 315, 316 as a winding. The lower stator part 32 has exactly six lower poles 320 of which each caries a lower coil 321, 322, 323, 324, 325, 326 as a winding. In this variant, the number of the upper poles 310 is also equal to the number of the lower poles 320, wherein here the number of the upper poles 310 and the number of the lower poles 320 is respectively an even number, namely six. Both the upper poles 310 and the lower poles 320 are each arranged equidistantly with respect to the peripheral direction, that is the angle between adjacent poles 310, 320 amounts in each case to 60° both in the upper stator part 31 and in the lower stator part 32.

Figure 16:
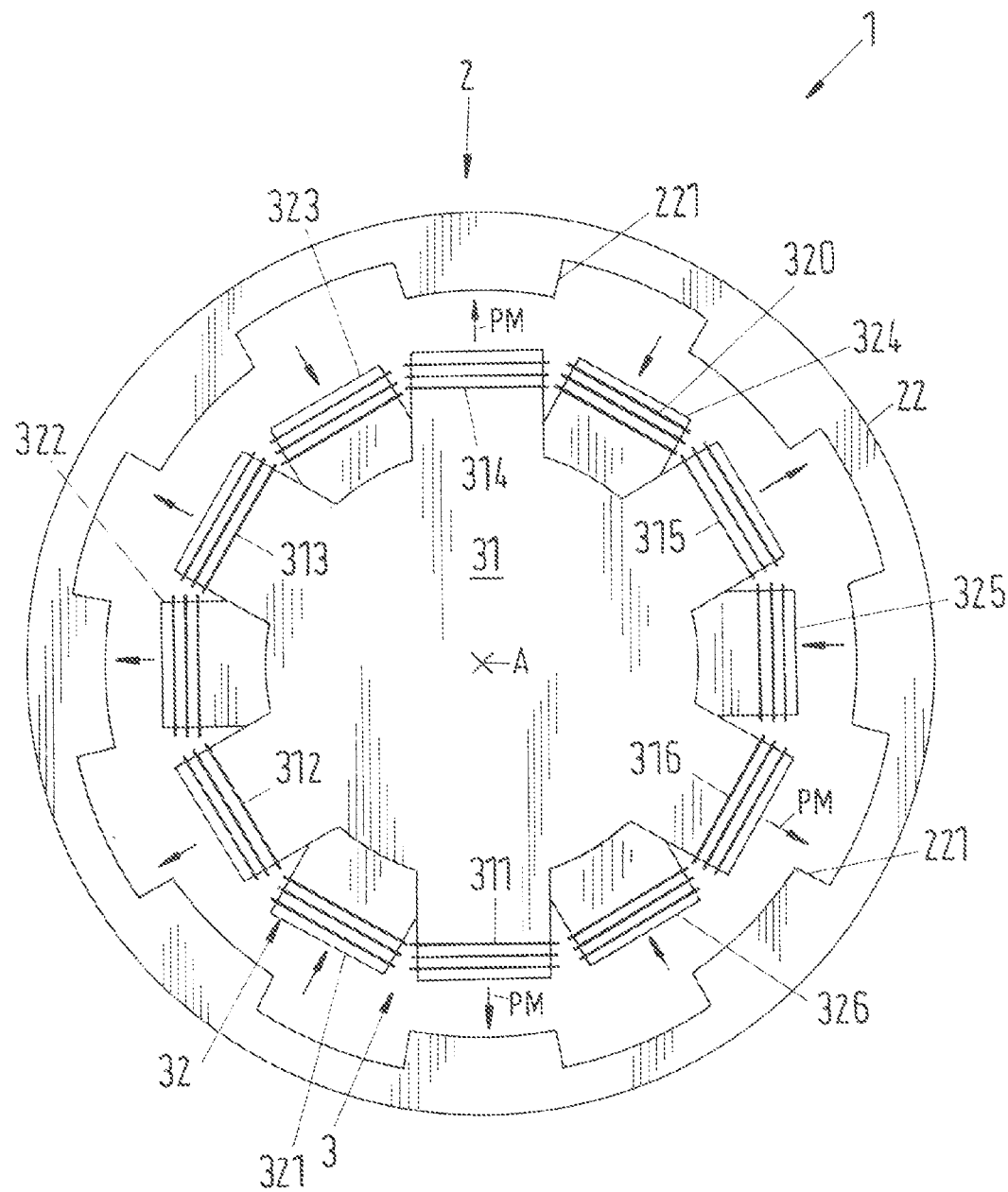
FIG. 16 is a plan view of the stator of FIG. 15 together with the magnetically active core of the rotor.

The substantially identically configured upper and lower stator parts 31 and 32 are arranged rotated relative to one another by an angle α=30° with respect to the desired axis of rotation A in the variant shown in FIG. 15 and FIG. 16 so that the upper poles 310, viewed in the axial direction, are each arranged in a gap between two adjacent lower poles 320. Since here the relationship α=360°/N is satisfied with N=12, each upper pole 310 is arranged, viewed in the axial direction, exactly centrally between two respective adjacent poles 320 of the lower stator part 32.

The setting device for controlling the stator 3 also comprises an amplifier unit 8 in the variant shown in FIG. 15 and FIG. 16, said amplifier unit having a separate power amplifier 81 for each of the twelve coils 311, 312, 313, 314, 315, 316, 321, 322, 323, 324, 325, 326 and the coil current for each of the coils can be regulated by said power amplifier independently of the coil currents of the respective other coils.

As already explained in connection with FIG. 3, it is also possible here that each separate power amplifier is respectively configured as an H bridge circuit in accordance with FIG. 3, wherein twelve H bridges are naturally then provided as power amplifiers 81 for the variant described here.

Figure 17A:
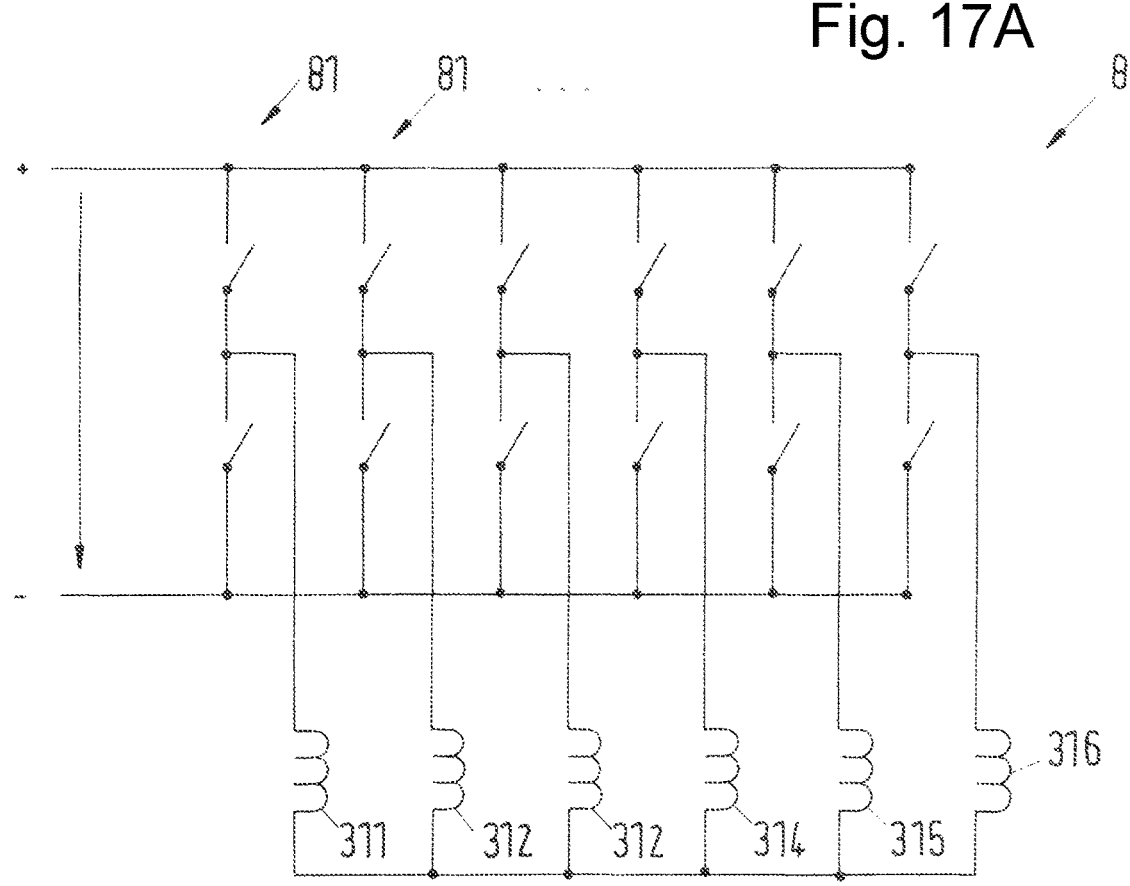
FIG. 17A and FIG. 17B are as FIG. 12, but for the stator in accordance with FIG. 16.
Figure 17B:
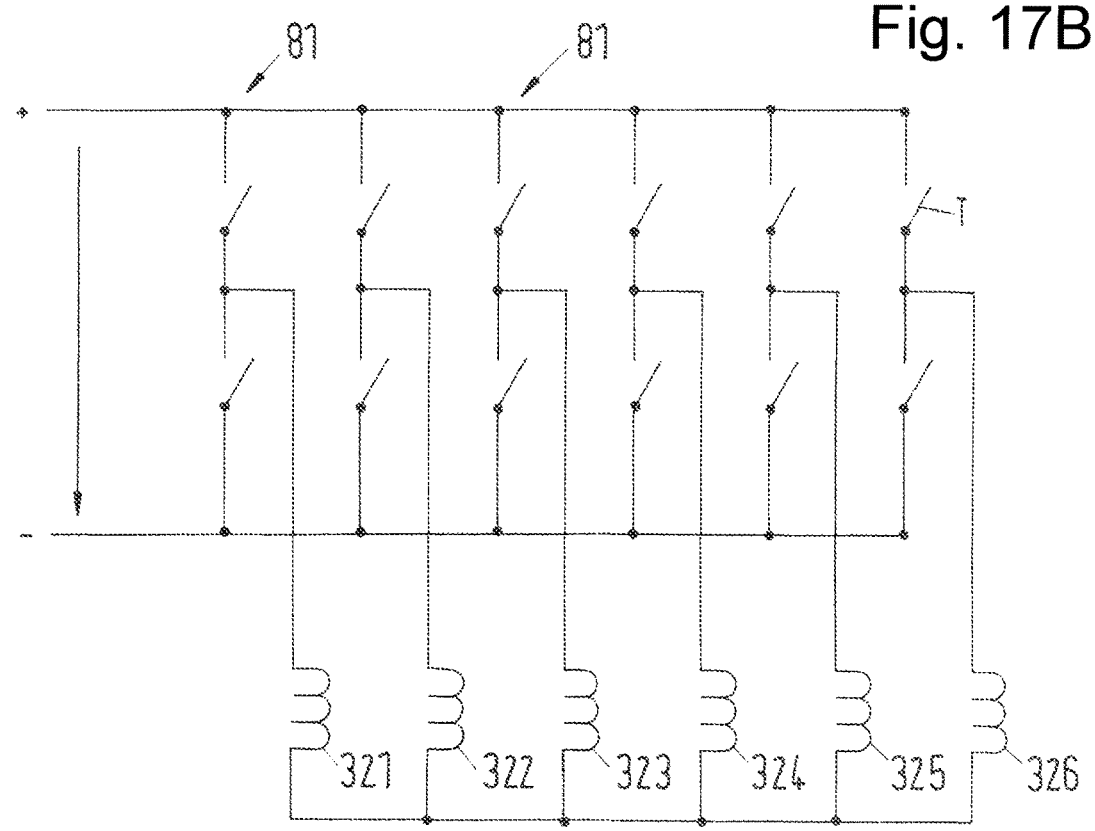

Alternatively, each power amplifier 81 can here also be configured as a respective bridge branch of an amplifier unit 8, in analogously the same manner as has been explained in connection with FIG. 4. The corresponding circuit is shown in FIG. 17A and FIG. 17B. The neutral point SP is here also preferably, but not necessarily, configured as a loadable neutral point.

In the variant shown in FIG. 15 or FIG. 16, it is also possible to connect two respective coils together to an electrical phase, whereby the number of required power amplifiers reduces because a separate power amplifier 81 is only required for each electrical phase.

The respective oppositely disposed coils are preferably connected together pairwise in each case in the upper stator part 31 and in the lower stator part 32. The following coil pairs are therefore each connected together to form an electrical phase: In the lower stator part 32, the coil 321 is connected together with the coil 324, the coil 322 to the coil 325 and the coil 323 to the coil 326. In the upper stator part 31, the coil 311 is connected together with the coil 314, the coil 312 to the coil 315 and the coil 313 to the coil 316.

Figure 18:
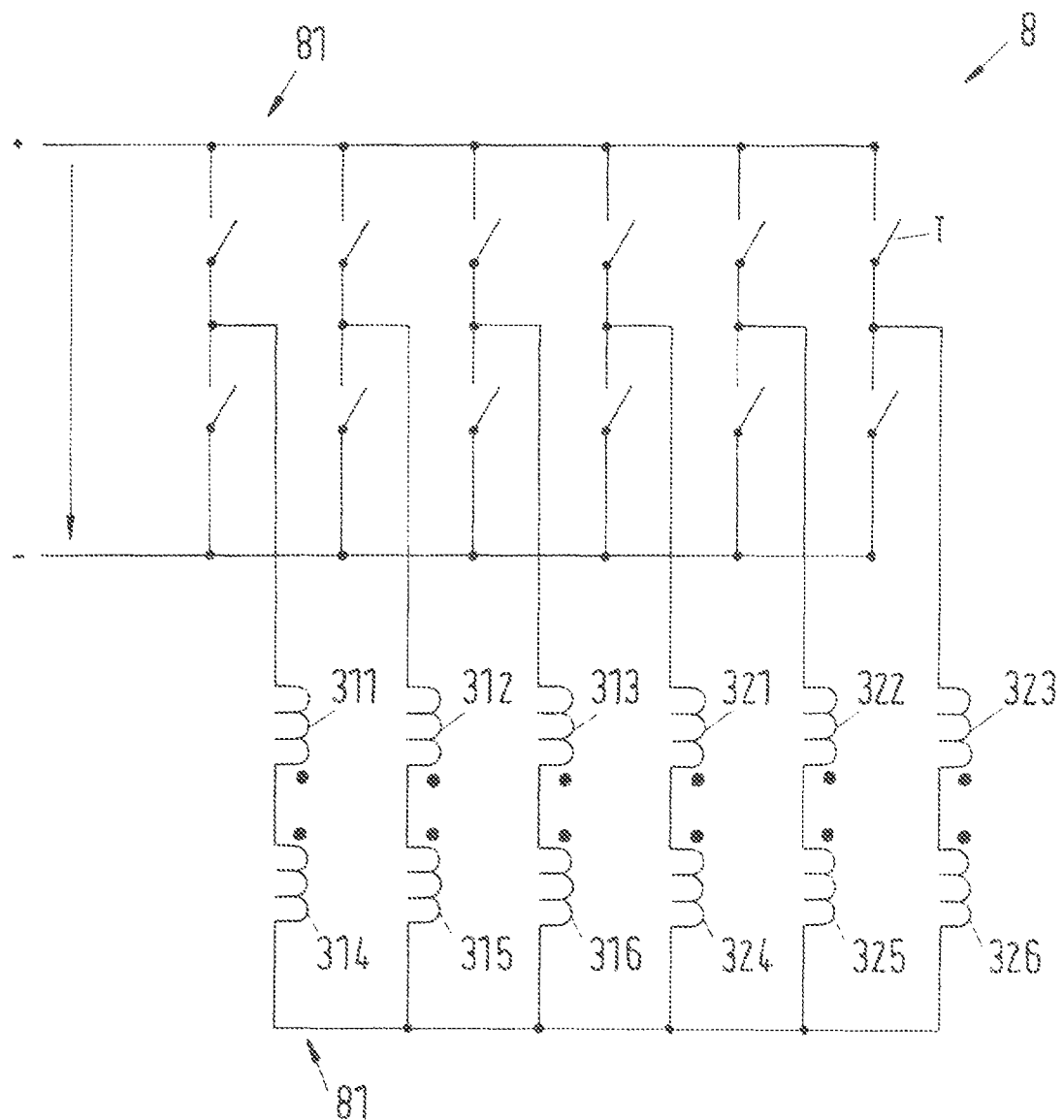
FIG. 18 is as FIG. 14, but for the stator in accordance with FIG. 16.

The corresponding circuit diagram with the separate power amplifiers 81 for each electrical phase is shown in FIG. 18 for the variant with bridge branches. In the circuit shown in FIG. 18, it is advantageous, but not necessary that the neutral point SP is loadable.

Figure 19:
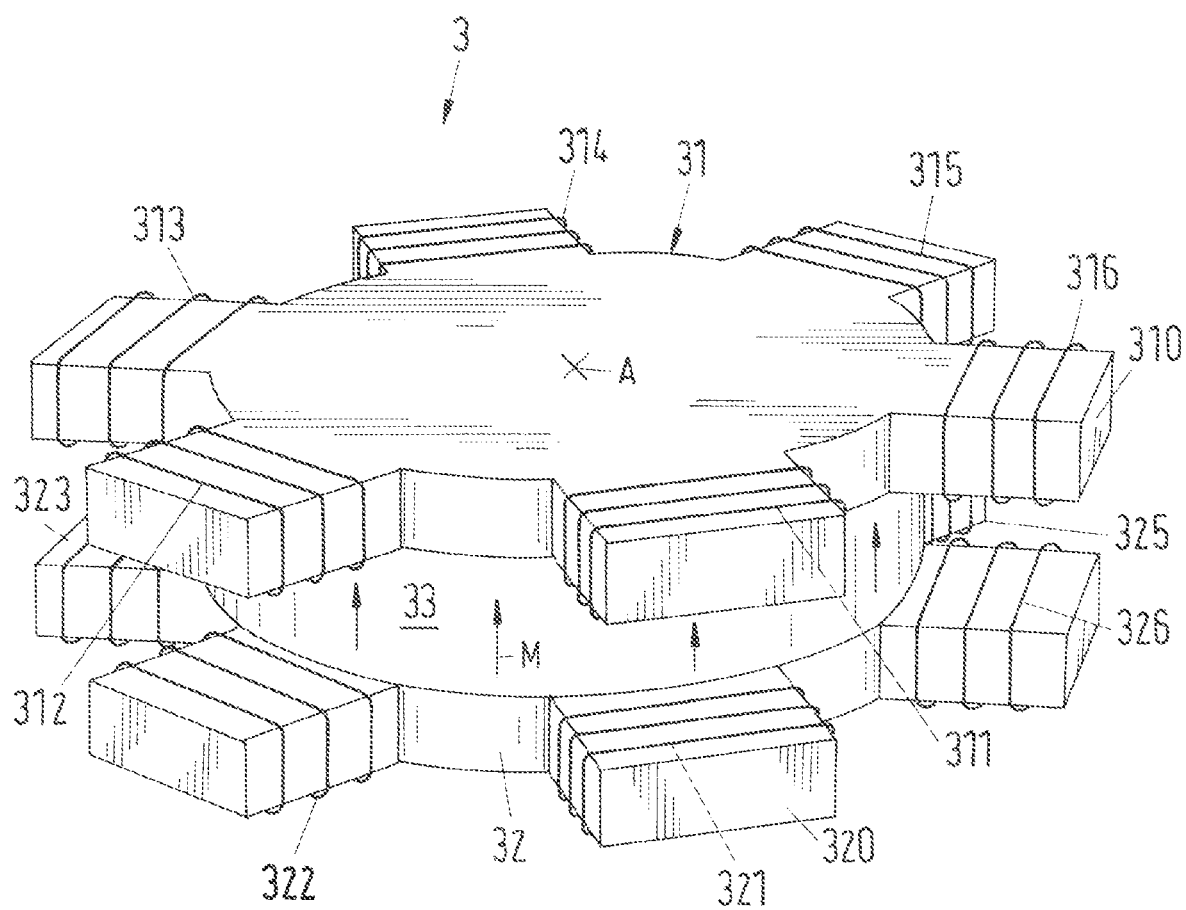
FIG. 19 is a perspective view of a fourth variant for the design of the stator of the first embodiment.

FIG. 19 shows in a perspective view a fourth variant for the configuration of the stator 3 of the first embodiment. For a better understanding, FIG. 20 shows a plan view from an axial direction of the stator 3 of FIG. 19 together with the magnetically active core 22 of the rotor 2.

The upper stator part 31 has exactly six upper poles 310 of which each caries an upper coil 311, 312, 313, 314, 315, 316 as a winding in this variant. The lower stator part 32 has exactly six lower poles 320 of which each caries a lower coil 321, 322, 323, 324, 325, 326 as a winding. In this variant, the number of the upper poles 310 is therefore also equal to the number of the lower poles 320, wherein the number of the upper poles 310 and the number of the lower poles 320 is respectively an even number, namely six. Both the upper poles 310 and the lower poles 320 are each arranged equidistantly with respect to the peripheral direction, that is the angle between adjacent poles 310, 320 amounts in each case to 60° both in the upper stator part 31 and in the lower stator part 32.

Figure 20:
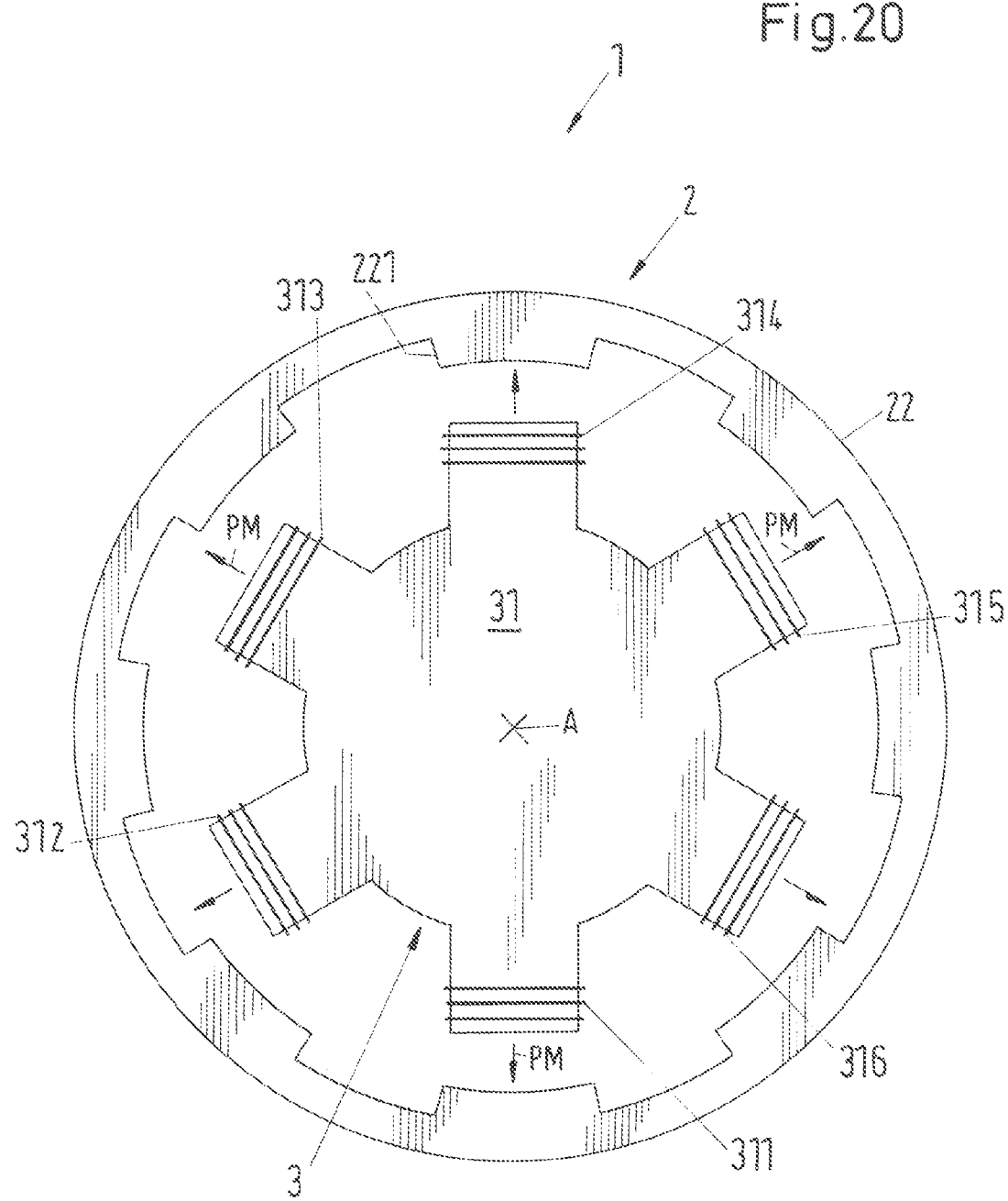
FIG. 20 is a plan view of the stator of FIG. 19 together with the magnetically active core of the rotor.

The substantially identically configured upper and lower stator parts 31 and 32 are not rotated relative to one another with respect to the desired axis of rotation A in the variant shown in FIG. 19 and FIG. 20, that is the angle α is equal to 0°. The upper poles 310 and the lower poles 320 are consequently arranged such that they overlap viewed in the axial direction. It is possible in this embodiment of the stator 3 also to stabilize the rotor 3 actively magnetically against tilts toward the radial plane so that now these two degrees of freedom of the tilt also be actively magnetically regulated. It is, however, necessary for this purpose that the coil current for each of the total twelve coils can be respectively regulated independently of the coil current for the other coils.

In the variant shown in FIG. 19 or FIG. 20, it is also possible to connect two respective coils together to an electrical phase, whereby the number of required power amplifiers reduces because a separate power amplifier 81 is only required for each electrical phase. In addition to the above-described connecting together of two respective coils of the upper or of the lower stator part 31, 32, it is also possible in the variant shown in FIG. 19 and FIG. 20 to connect together a respective coil of the lower stator part 32 with a coil of the upper stator part 31. In this respect, the coils respectively lying above one another with respect to the axial direction are connected together. The coil 311 is then therefore connected to the coil 321, the coil 312 to the coil 322, the coil 312 to the coil 323, the coil 314 to the coil 324, the coil 315 to the coil 325 and the coil 316 to the coil 326.

Figure 21:
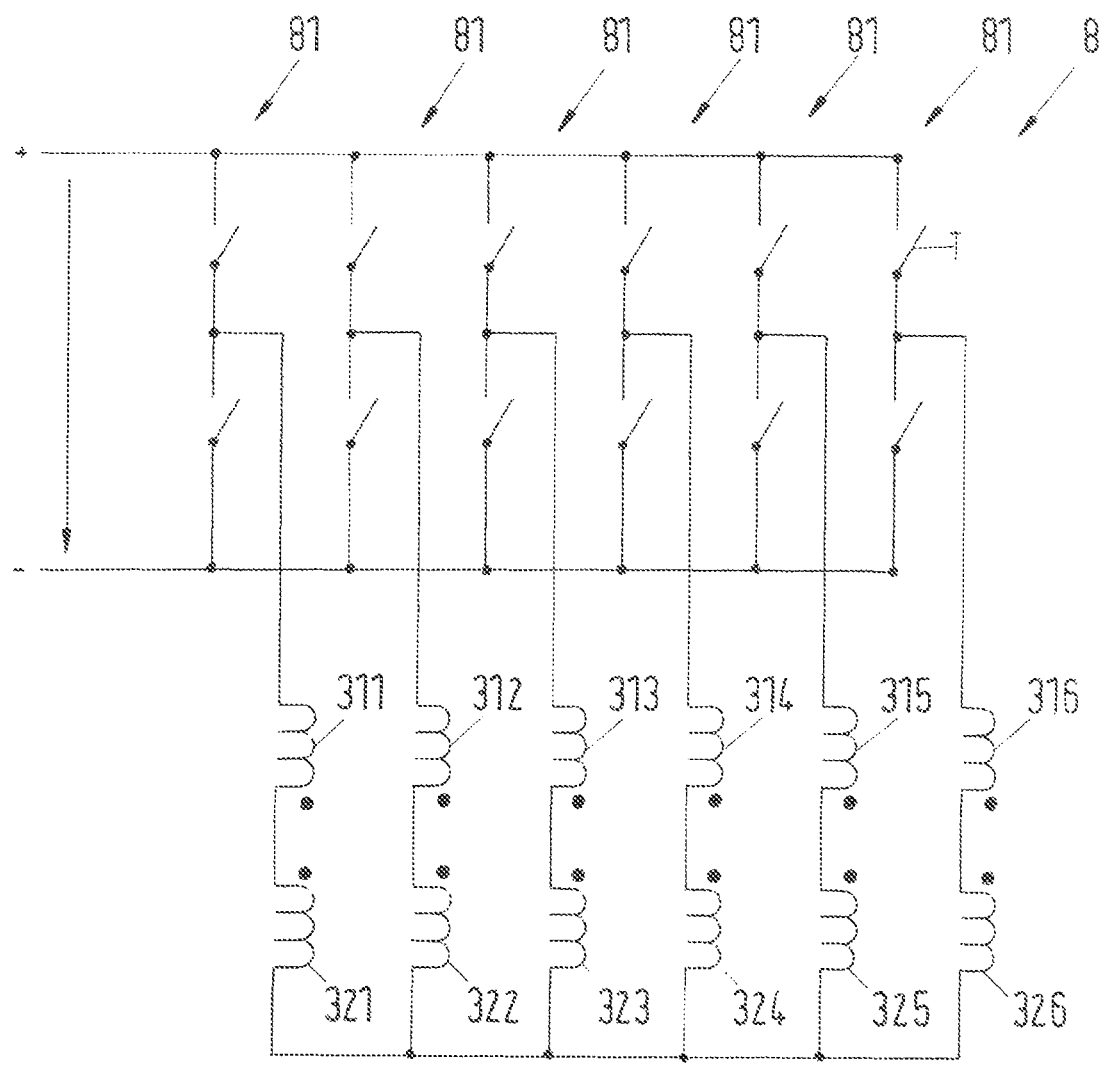
FIG. 21 is as FIG. 18, but for the stator in accordance with FIG. 20.

The corresponding circuit diagram with the separate power amplifiers 81 for each electrical phase is shown in FIG. 21 for the variant with bridge branches. In the circuit shown in FIG. 21, it is advantageous, but not necessary, that the neutral point SP is loadable.

On the connecting together of two respective coils, only a connecting together of the coils in series is described above. It is, however, understood that the coils can also be connected together in a parallel circuit.

Figure 22:
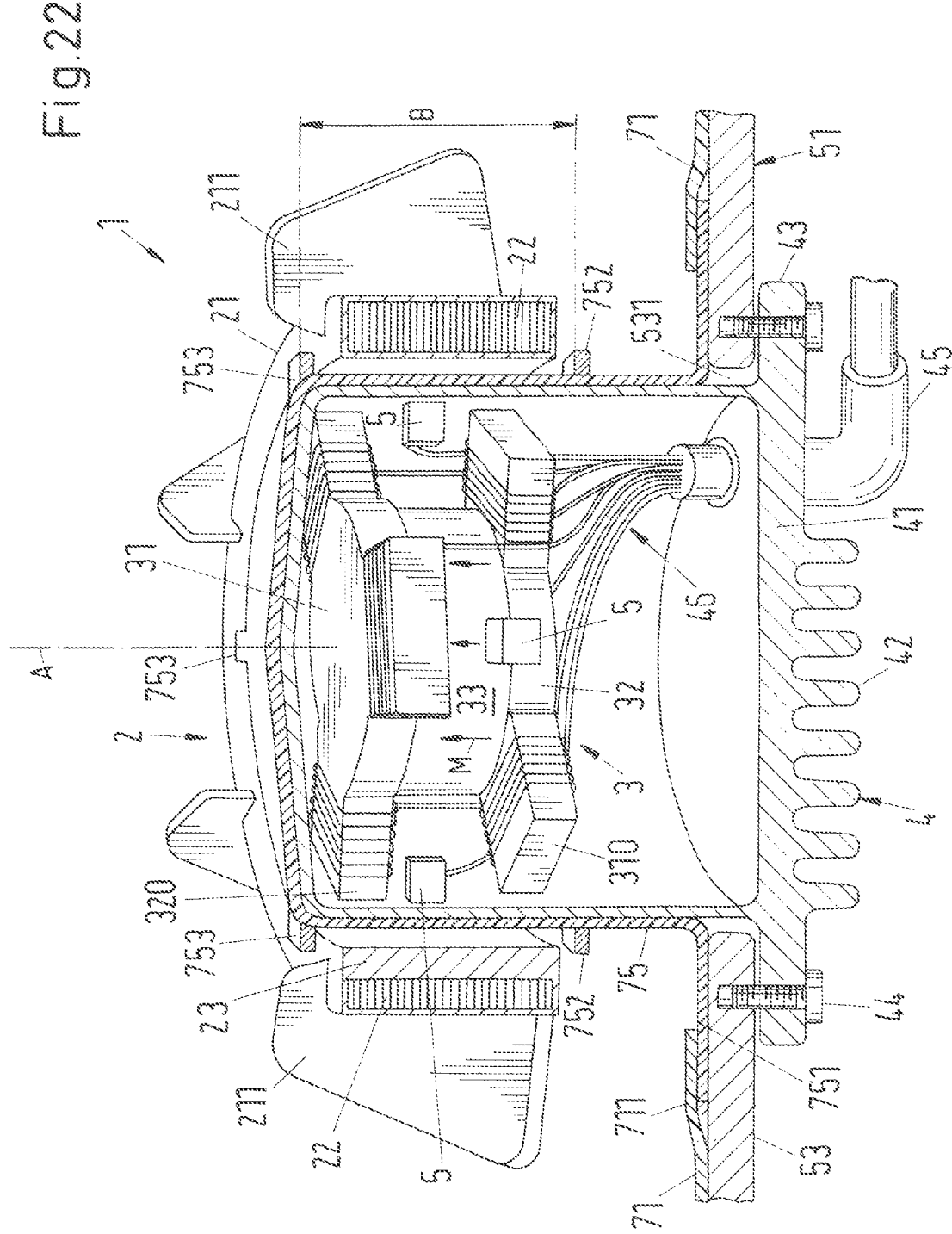
FIG. 22 is a perspective sectional representation of a second embodiment of the rotary drive in accordance with the invention designed as a pumping or mixing apparatus.

FIG. 22 shows in a perspective sectional representation a second embodiment of the rotary drive 1 in accordance with the invention which is configured as a pumping or mixing apparatus. In the following, only the differences from the above-described first embodiment will be looked at. The reference numerals in particular have the same meaning as has already been explained in connection with the first embodiment. It is understood that all above-described variants, embodiments and measures can also be realized in the same manner or in analogously the same manner in the second embodiment.

Such configurations of the rotary drive 1 in accordance with the invention as a pumping or mixing apparatus can be used, for example, in the pharmaceutical industry and in the biotechnological industry. This configuration is specifically suitable for such applications in which a very high degree of purity or sterility of those components is key which come into contact with the substances to be mixed. This configuration of the rotary drive 1 in accordance with the invention can also be formed as a bioreactor or as a fermentor. It is, however, understood, that this configuration can also very generally be a pumping or mixing apparatus with which media or substances can be mixed. These substances can in particular be fluids or solids, preferably powders. Such pumping or mixing apparatus are suitable for mixing liquids among one another and/or for mixing of at least one liquid with a powder or other solid and/or for mixing gases with liquids and/or solids.

In the second embodiment shown in FIG. 22, the electromagnetic rotary drive 1 configured as a pumping or mixing apparatus comprises a flexible mixing tank 71 for receiving the substances to be mixed which is manufactured from a plastic and which is only indicated in FIG. 22. The mixing tank 71 is preferably a flexible pouch, for example a plastic sack or a sack of a synthetic material, which can be folded together so that is takes up as little space as possible during storage. The mixing tank 71 is placed into a support tank 51 which is likewise only indicated in FIG. 22 and which supports the mixing tank 71.

The mixing tank 71 has in its base region a substantially cylindrical bucket 75 which extends in the inner space of the mixing tank 71 and is arranged at the center of the base region. The cylindrical bucket 75 is preferably stable in shape and produced from a plastic. It can also be formed in the form of a flexible hose, for example.

The rotor 2 which comprises an impeller 21 having a plurality of blades for mixing the substances is arranged in the mixing tank 71. So that the rotor 2 can be magnetically contactlessly driven—that is can be set into rotation—it comprises a magnetically active core 22 (see also FIG. 1 and FIG. 2 in this respect) which is arranged radially inwardly disposed with respect to the impeller 21. The rotor 2 has a substantially ring-shaped design with a central opening so that it is arranged, in the position of use which is shown in FIG. 22, around the bucket 75 which is then located in the central opening of the rotor 2.

The substantially cylindrically configured support tank 51 is open at its upper side so that the mixing tank 71 can be introduced into the support tank 51 without problem.

The support tank 51 has at its base 53 a centrally arranged separating can 4, which is substantially cylindrical in shape, for receiving the stator 3. The separating can 4 extends in the direction of its cylinder axis, which typically coincides with the desired axis of rotation A, upwardly in accordance with the representation so that it is arranged coaxially in the bucket 75 of the mixing tank 71 in the assembled state. The dimensions of the separating can 4 and of the bucket 74 are adapted to one another in this respect such that the bucket 75 tightly surrounds the separating can 4 in the assembled state and its jacket surface contacts the jacket surface of the separating can 4.

The stator 3 is arranged in the separating can 4 and the rotor 2 can be driven contactlessly by it about a desired axis of rotation A in the operating state and can be magnetically contactlessly supported with respect to the stator 3.

The assembly of the mixing tank 71 with the rotor 3 contained therein and of the support tank 51 can be carried out extremely simply, fast and in particular without tools. For this purpose, the mixing tank 71, which is typically folded together for storage, is removed from its packaging together with the rotor 2 located therein, is placed into the support tank 51 and the bucket 75 with the rotor 2 disposed around it is pushed over the separating can 4. The rotary drive 1 configured as a pumping or mixing apparatus is then already ready for use. After use, the mixing tank 71 with the bucket 75 and the rotor 2 is simply pulled out of the support tank 51. The bucket 72 in this respect simply releases from the separating can 4. This particularly simple and problem-free connection and separation in particular also makes this second embodiment usable for single use, with then the mixing tank 71 and the rotor 2 being able to be configured for single use, whereas the support tank 51 and the stator 3 with the separating can 4 are designed for permanent use or multiple use.

The stator 3 in this embodiment is poured by thermally conductive compound in the separating can 4 and is thus fixed in the separating can 4. The separating can 4 is closed in accordance with the illustration at the bottom by a can base 41 which has a plurality of cooling ribs 42. The can base 41 comprises a radially outwardly disposed flange 43 which serves for the fastening of the separating can 4 at the base 53 of the support tank 51. The base 53 has a centrally arranged circular opening 531 which is dimensioned such that the separating can 4 can be pushed in accordance with the illustration from below through the opening 531 into the inner space of the support tank 51 and can then be fixed at the base 53 of the support tank 51 by screws 44 which engage through the flange 43. The can base 41 has a bore through which a line 45 extends into the inner space of the separating can 4. All the electrical connections which are required for the energy supply and the control of the stator 3 as well as for the data exchange between sensors and measuring devices using the control and regulation device, not shown, are collected in the line 45. These electrical connections are provided as a whole with the reference numeral 46. The separating can 4 can be produced from a metallic material or from a plastic.

A variant to the fixed connection between the separating can 4 and the support tank 51 comprises the separating can 4 only being introduced in accordance with the illustration from below into the bucket 75 after the placing of the mixing tank 71. This introduction can take place either by hand or also by a lifting device which moves the separating can 4 through the opening 531 into the bucket 75 and then holds it in this position. No separate fixing of the separating can 4 to the support tank 51 is necessary in this variant. After use, the lifting device then moves the separating can 4 back down in accordance with the illustration (FIG. 22).

Since the bucket 75 of the mixing tank 71 is preferably configured in stable shape, but the remainder of the mixing tank 71 configured as a pouch typically is not, it is advantageous, but not absolutely necessary, to manufacture the bucket 75 as a separate part and subsequently to connect it to the mixing tank 71. A possibility for this is in particular also shown in FIG. 22. The shape-stable, substantially cylindrical bucket 75 is manufactured as a separate part, for example using an injection molding process, having a flange 751 extending along the periphery at its end at the bottom in accordance with the illustration—that is at the open end— and extending in the radial direction. The remainder of the mixing tank 71 configured as a pouch has a circular opening whose diameter is smaller than the diameter of the flange 751. The bucket 75 is then introduced into the mixing tank 71 so that the margin 711, which bounds the circular opening, lies on the flange 751 of the bucket 75 and overlaps with it. Subsequently, the bucket 75 is welded or adhesively bonded to the mixing tank in the region of the overlap between the flange 751 and the margin 711 so that the weld seam or bond seam connects the bucket 75 firmly and unreleasably to the mixing tank 71.

A plurality of upper holding elements 753 and lower holding elements 752 are preferably arranged distributed over the periphery of the bucket 75 at the outer jacket surface of the bucket 75. A respective four upper and lower holding elements 753 and 752 respectively are provided in the variant shown. Each holding element 752, 753 is respectively configured as a nub which extends away from the desired axis of rotation A in the radial direction. In this respect, a respective upper holding element 753 and a lower holding element 752 are arranged pair-wise such that they are aligned with one another with respect to the axial direction and are remote from one another by a distance B. The distance B is selected in this respect such that the rotor 2 fits between the upper and the lower holding elements 753 and 752 with a considerable clearance with respect to the axial direction. The length of the holding elements 752 and 753 in the radial direction is dimensioned such that the movement possibility of the rotor 2 in the axial direction is restricted by the holding elements 753 and 752 respectively. The rotor 2 can therefore only move in the axial direction between the holding elements 753 and 752. This measure is in particular advantageous for the storage of the mixing tank 75 prior to use and for the insertion of the mixing tank 75 with the rotor 2 located therein into the support tank 51 because the rotor 2 is thus held approximately in the position which it should adopt during operation. The holding elements 753, 752 have no function during the operation of the mixing apparatus 1.

The rotor 2 comprises the magnetically active core 22 and the impeller 21 and is configured free of coils, i.e. no windings are provided on the rotor 2. In a very especially preferred embodiment, which is also realized in the embodiment described here, the rotor 2 or the magnetically active core 22 of the rotor 2 does not have any permanent magnets; it is therefore free of permanent magnets. This measure allows a particularly inexpensive embodiment of the rotor 2, which in particular represents a large advantage in a configuration of the rotor 2 as a single-use part. For no rare earths such as neodymium or samarium, or compounds or alloys thereof, which are frequently used for the manufacture of permanent magnets, are required for the manufacture of the rotor 2. The dispensing with of these permanent magnets also signifies a large advantage under environmental aspects.

The rotor 2 furthermore has the impeller 21 having a plurality of blades 211 distributed over the periphery of the rotor 2 which can blend the substances in the mixing tank 71. The impeller 21 is arranged radially outwardly disposed with respect to the magnetically active core 22, wherein the blades 211 are arranged substantially at the same height with respect to the axial direction as the magnetically active core 22.

The rotor 2 is configured as an integral rotor because it is both the rotor 2 of the electromagnetic drive 1 and the rotor of the magnetic bearing and the rotor 2 of the mixer. This offers the advantage of a very compact and space-saving design.

The magnetically active core 22 has a jacket 23 which comprises a plastic and which completely surrounds the magnetically active core 22. The magnetically active core is preferably cast into a plastic which forms the jacket 23. The blades 211 can, for example, be placed onto the jacket 23 and can be fixed there by a clamping connection or can be adhesively bonded or welded to the jacket 23. It is also possible that the blades 211 are an integral component of the jacket 23.

When the rotor 2 and the mixing tank 71 are designed for single use, the parts produced from plastic should be manufactured from a commercial plastic which is as inexpensive as possible. A further essential aspect in the configuration for single use is that the single-use parts have to be able to be sterilized for certain areas of application. In this respect, it is particularly advantageous if the single-use parts can be gamma sterilized. In this type of sterilization, the element to be sterilized is acted on by gamma radiation. The advantage of the gamma sterilization, for example in comparison with steam sterilization, in particular lies in the fact that the sterilization can also take place through the packaging. It is common practice especially with single-use parts that the parts are brought into the packaging provided for shipping after their manufacture and are then stored for some time before they are delivered to customers. In such cases, the sterilization takes place through the packaging only shortly before the delivery to the customer, which is not possible with a steam sterilization or with other methods.

It is as a rule not necessary that the single-use parts—such as the mixing tank 71 and the rotor 2—have to be able to be sterilized more than once. This is in particular a great advantage with the gamma sterilization because the application of gamma rays to plastics can result in degradations so that a multiple gamma sterilization can make the plastic unusable.

Since as a rule a sterilization at high temperatures and/or at a high (steam) pressure can be dispensed with for single-use parts, less expensive plastics can be used, for example those which cannot withstand high temperatures or which cannot be exposed to high temperature values and high pressure values a multiple of times.

When taking all these aspects into account, it is therefore preferred in the configuration for single use to use those plastics for the manufacture of the single-use apparatus which can be gamma sterilized at least once. The materials should in this respect be gamma-stable for a dose of at least 40 kGy to allow a single-time gamma sterilization. In addition, no toxic substances should arise in the gamma sterilization. It is additionally preferred for all materials which come into contact with the substances to be mixed or the blended substances to satisfy USP Class VI standards.

The following plastics are, for example, preferred for the manufacture of the flexible mixing tank 71: Polyethylenes (PE), low density polyethylenes (LDPE), ultra low density polyethylenes (ULDPE), ethylene vinyl acetates (EVA), polyethylene terephthalates (PET), polyvinylchloride (PVC), polypropylenes (PP), polyurethanes (PU), silicones.

The following plastics are, for example, preferred for the manufacture of the bucket 75 and the parts of the rotor 2 comprising plastic, that is the impeller 21 and the jacket 23: Polyethylenes (PE), polypropylenes (PP), low density polyethylenes (LDPE), ultra low density polyethylenes (ULDPE), ethylene vinyl acetates (EVA), polyethylene terephthalates (PET), polyvinylchloride (PVC), polyvinylidene fluorides (PVDF), acrylonitrile butadiene styrenes (ABS), polyacrylics, polycarbonates (PC).

Less suitable materials or even unsuitable materials for the manufacture of the plastic parts are, for example, the materials polytetrafluroethylenes (PTFE) and perfluooralkoxy polymers (PFA) known under the brand name Teflon. There is namely the risk with these materials on gamma sterilization that hazardous gases arise such as fluorine which can then form toxic or harmful compounds such as hydrofluoric acid (HF). Such materials can naturally be used in such applications in which especially the rotor 2 is not designed for single use.

Figure 23:
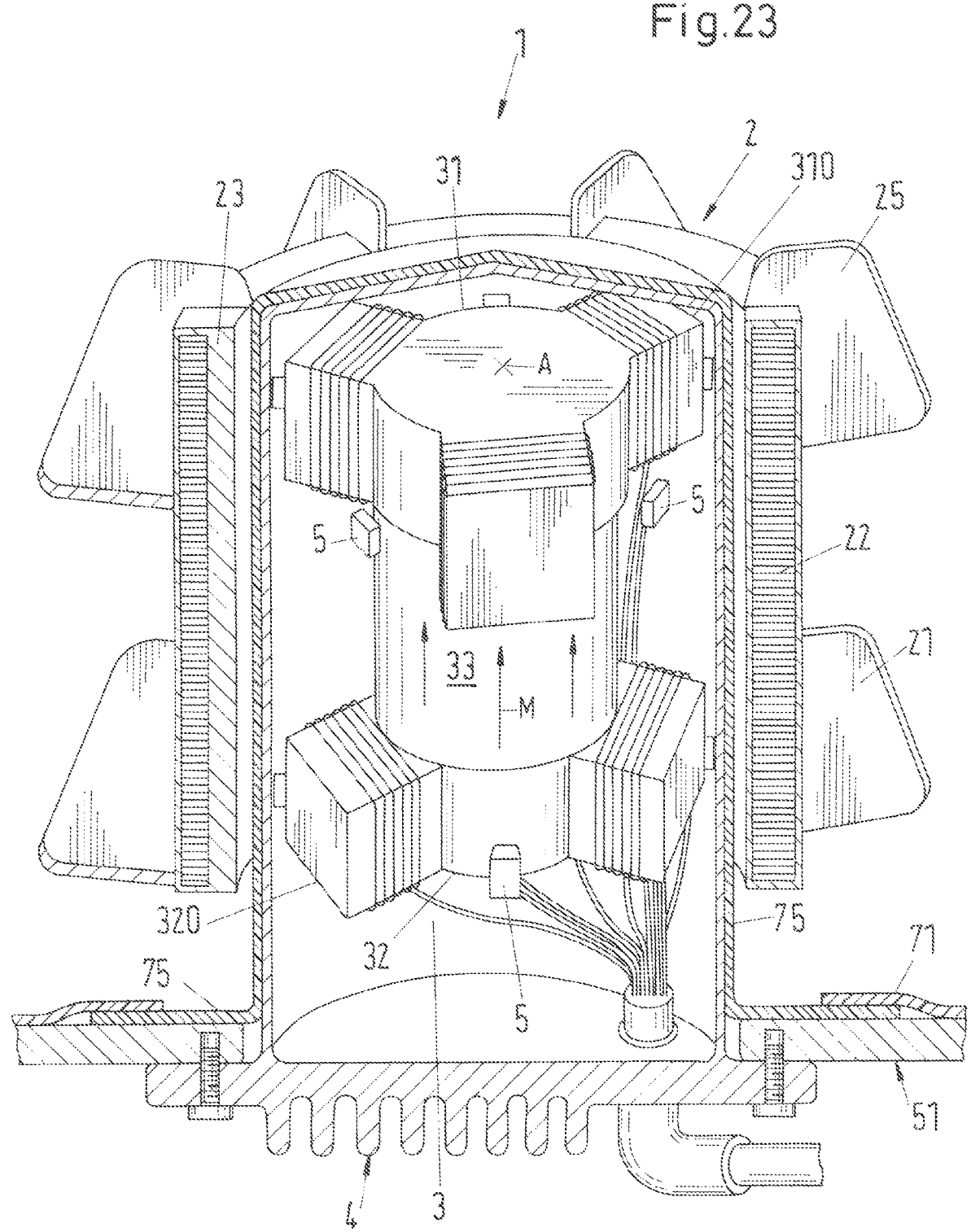
FIG. 23 is a perspective sectional representation of a third embodiment of the rotary drive in accordance with the invention designed as a pumping or mixing apparatus.

FIG. 23 shows in a representation analog to FIG. 22 a perspective sectional representation of a third embodiment of a rotary drive 1 in accordance with the invention which is configured as a pumping or mixing apparatus. In the following, only the differences from the above-described first and second embodiments will be looked at. The reference numerals in particular have the same meaning as has already been explained in connection with the first and second embodiments. It is understood that all the above-described variants, embodiments and measures can also be realized in the same manner or in analogously the same manner in the third embodiment.

In the embodiment shown in FIG. 23, the rotor 2 has two impellers 21, 25 for mixing the substances which are arranged spaced apart from one another with respect to the axial direction. Both impellers 21 and 25 are components of the only rotor 2 and are each provided radially outwardly disposed at the magnetically active core 22 of the rotor.

In comparison with the second embodiment, the stator 3 in the second embodiment has a greater height in the axial direction. This can be implemented, for example, in that the extent of the permanent magnet 33 of the stator 3 is increased in the axial direction so that the spacing between the lower stator part 32 and the upper stator part thus also increases or in that the axial height of the lower and/or upper stator part 32, 31 is increased, or by a combination of these two measures. The rotor 2 and the stator 3 are preferably configured such that the one impeller 21 is arranged at the same height (in the axial direction) as the lower stator part 32 in the operating state and the other impeller 25 is arranged at the same height as the upper stator part 32.

The magnetically active core 22 of the rotor 2 is here also preferably configured substantially in ring shape or cylinder shape and extends substantially over the total axial height of the rotor 2.

Unlike the second embodiment, in the third embodiment, position sensors 5 are provided both in the region of the lower stator part 32 and in the region of the upper stator part 31 so that tilts of the rotor 3 with respect to the radial plane can be detected.

It is in particular preferred in the third embodiment that each of the coils of the lower stator part 32 and each of the coils of the upper stator part 31 can be controlled separately so that the rotor 3 can be actively magnetically regulated with respect to tilts toward the radial plane (two degrees of freedom). It is understood that the two stator parts 31, 32 can also have more than three coils and poles, in particular also four, five or six coils and upper poles 310 and lower poles 320.

It is understood that more than two impellers 21, 25 can also be provided on the rotor.

Figure 24:
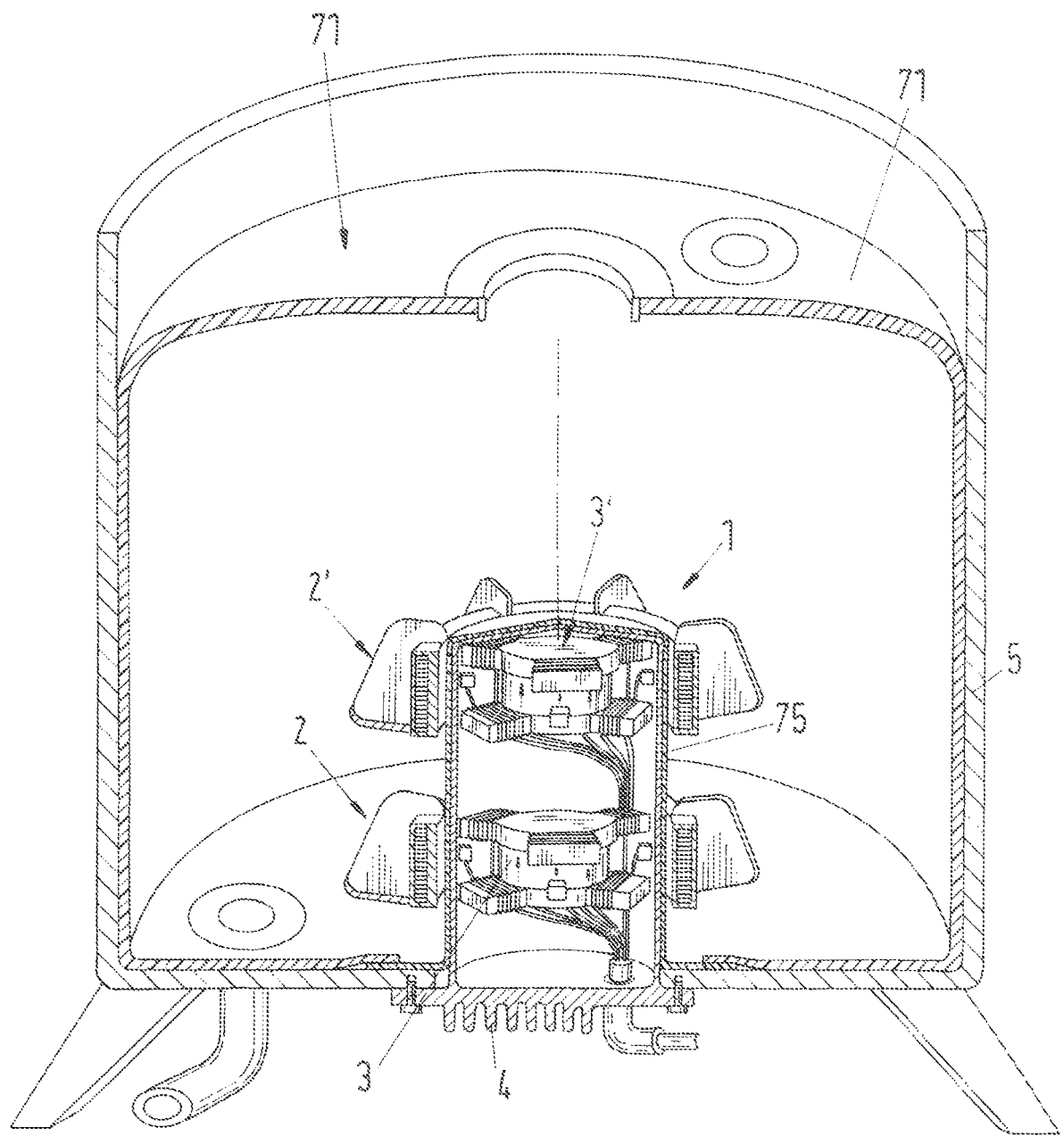
FIG. 24 is a perspective sectional representation of a fourth embodiment of the rotary drive in accordance with the invention integrated into a mixing apparatus.
Figure 25:
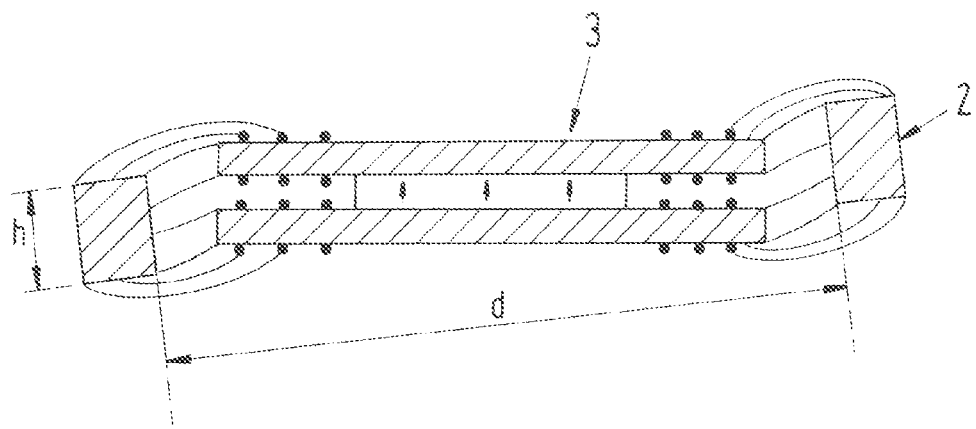
FIG. 25 is a schematic representation for illustrating the passive magnetic stabilization of the rotor against tilts.
Figure 26:
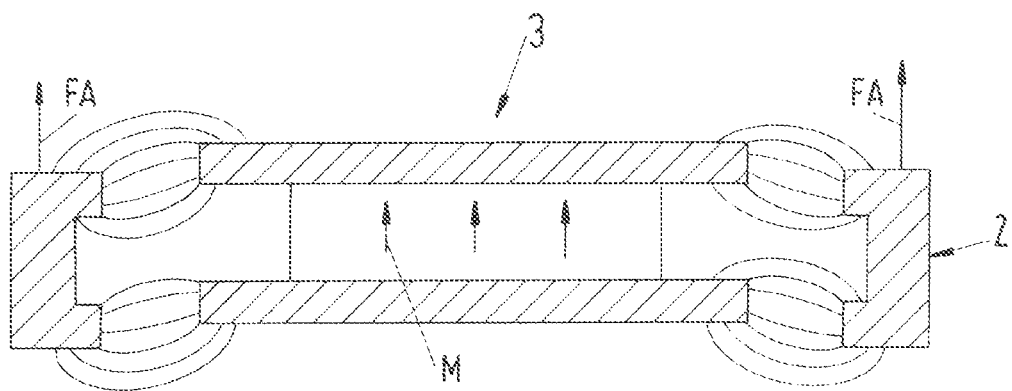
FIG. 26 is a schematic representation for illustrating the passive magnetic stabilization of the axial position of the rotor.

FIG. 24 shows in a perspective sectional representation a fourth embodiment of the rotary drive 1 in accordance with the invention which is integrated into a mixing apparatus. In the following, only the differences from the above-described first, second and third embodiments will be looked at. The reference numerals in particular have the same meaning as has already been explained in connection with the first, second and third embodiments. It is understood that all the above-described variants, embodiments and measures can also be realized in the same manner or in analogously the same manner in the fourth embodiment. The fourth embodiment is characterized in that the rotary drive comprises two rotors 2, 2' which are provided in the mixing tank 71 and of which each respectively comprises an impeller 21, 21' for mixing the substances. Each rotor 2, 2' can here also respectively be magnetically contactlessly driven and is free of coils and free of permanent magnets in each case. In the operating state, the two rotors 2, 2' are arranged spaced apart with respect to the axial direction and coaxially, i.e. they have the same desired axis of rotation A.

Two stators 3, 3' are furthermore provided of which each is configured in accordance with one of the above-described embodiments. Both stators 3, 3' are arranged in the separating can 4 and are spaced apart from one another axially. The lower stator 3 in accordance with the illustration is associated with the lower rotor 2 in accordance with the illustration and forms with it an electromagnetic rotary drive which is configured according to the principle of the bearingless motor. The upper stator 3' in accordance with the illustration is associated with the lower rotor 2' in accordance with the illustration and forms with it an electromagnetic rotary drive which is configured according to the principle of the bearingless motor.

The two rotors 2, 2' are likewise configured in accordance with one of the above-described embodiments. The two rotors 2, 2' can be configured as substantially the same or also differently.

The same applies to the two stators 3, 3'. They can also be configured substantially the same or also differently, for example with a different number of lower or upper poles 320, 310.

The special advantage of the fourth embodiment lies in the fact that considerably more mixing procedures can hereby be realized; it is thus possible, for example, that the two rotors 2, 2' rotate in different directions and/or at different speeds of rotation.

In the above-described embodiments, variants and measures, reference is made to such cases in which the lower stator part 32 has the same number of lower poles 320 as the upper stator part 31 has upper poles 310. This is naturally by no means necessarily so. Embodiments are by all means also possible in which the number of upper poles 310 is different than the number of lower poles 320.

The stator 3 and the rotor 2 together form the electromagnetic rotary drive 1 which, as already explained, preferably works according to the principle of the bearingless motor. In a bearingless motor, at least three degrees of freedom of the rotor, namely its rotation about the desired axis of rotation A and its position in the radial plane, can always be actively magnetically regulated. The degree of freedom of the axial position of the rotor 3 is passively magnetically stabilized in the rotary drive in accordance with the invention, that is no separate axial magnetic bearing or mechanical axial bearing is required. On the one hand, the rotor 2 thereby becomes particularly simple and inexpensive and, on the other hand, the rotor 2 can be simply separated from the stator 3 and, optionally, from the separating can 4. Due to the lack of axial bearing components, the rotor 2, which is restricted in its freedom of movement with respect to the axial direction of the configuration in accordance with FIG. 22 at most only via the holding elements 752, 753 connected to the bucket 75, can namely be drawn together with the bucket 22 simply axially from the separating can 4 or from the stator 3. The magnetically active core 22 of the rotor 2 is in this respect drawn back as by magnetic spring forces on deflection in the axial direction by the magnetic fields emanating from the stator. This is illustrated in the very schematic representation in FIG. 28. If the rotor 3 is moved out of the desired position, that is out of the radial plane, with respect to its axial position (downwardly in accordance with the illustration in FIG. 28), this effects passively magnetically axial restoring forces, represented by the arrows FA in the axial direction, which move the rotor 2 after the disappearance of the other external forces back into its desired position with respect to the axial direction.

In this respect, the forces FA first increase with the deflection, reach a maximum at a specific deflection which depends on the geometry of the magnetically active core 22 of the rotor 2, on the geometry of the upper stator part 31 and of the lower stator part 32, on the spacing between the upper stator part 31 and the lower stator part 32, on the geometry and the magnetic properties of the permanent magnet 33 and on the air gap (the spacing between the stator parts 31 and 32, on the one hand, and the magnetically active core 22 of the rotor 2, on the other hand) and then decrease again. In the bearingless motor for the rotary drive 1 in accordance with the invention, the characteristic of the inherent axial passive magnet bearing is selected such that the axial forces which act on the rotor 2 lie beneath the maximum force of the axial passive magnet bearing in the total operating range and such that, in such applications in which the rotor 2 should be able to be simply separated from the stator 3, the maximum force of the axial passive magnet bearing remains small enough for the rotor 2, optionally with the mixing tank 71, to be able to be separated easily and without tools from the separating can 4 and the stator 3. In this respect, a maximum force of the axial passive magnet bearing of a maximum of 200 Newtons has been found to be still manageable without tools or an auxiliary apparatus for configurations as a pumping or mixing apparatus. With smaller mixing apparatus, a considerably smaller maximum force of the axial passive magnetic bearing is selected to design the insertion and removal in as simple a manner as possible. Values between Newtons and 80 Newtons are typical for mixing apparatus for 50 liters to 1000 liters and for low-viscosity liquids.

A passively magnetic stabilization can likewise be realized for the two remaining degrees of freedom, namely the tilts of the rotor 2 relative to the radial plane, in all embodiments with the exception of that in accordance with FIG. 23. As already previously described, in such embodiments, the regulation of the bearingless motor becomes particularly simple and the number of power amplifier channels can also be reduced. How this can be realized in the bearingless motor of the mixing apparatus in accordance with the invention is illustrated in FIG. 27. On the tilting of the rotor 2 shown there, passively magnetic restoring forces arise which effect a torque due to their different directions at the left and right sides of the rotor 2 in accordance with the illustration, said torque counteracting the tilt so that the rotor 2 is also passively magnetically stabilized with respect to these two degrees of freedom. This passive stabilization, however, only works when specific geometric conditions are satisfied. If the inner diameter of the rotor 2 is marked by d and the height of the magnetically active core 22 of the rotor by h, the inner diameter must be at least 2.6 times as large as the height h. The condition d>2.6*h should then be satisfied, that is the inner diameter d should be larger than 2.6 times the height h.

For this reason, it is also preferred for the mixing apparatus 1 in accordance with the invention if the rotor 2 to be stabilized purely passively magnetically with respect to tilts toward the radial plane (two degrees of freedom), if the inner diameter of the rotor 2 is at least 2.6 times as large as the height h of the magnetically active core 22 in the axial direction.

In embodiments of the invention in which this geometrical condition is no longer satisfied, the rotor 2 is actively magnetically regulated with respect to these tilts.

In the above-described embodiments, variants and measures, reference is made to such cases in which the electromagnetic rotary drive 1 formed from the stator 3 and the rotor 2 is configured as an external rotor, that is with an inwardly disposed stator 3 and a rotor 2 arranged around it. It is understood that the invention is not restricted to such cases, but that, with the rotary drive 1 in accordance with the invention, the rotor 2 and the stator 3 can also form an electromagnetic rotary drive which is configured as an internal rotor, that is with an inwardly disposed rotor 2 and a stator 3 arranged around it.

For example, with reference to FIG. 22 or FIG. 24, such a configuration as an internal rotor can be realized e.g. such that the bucket 75 is not aligned into the mixing tank 71, but rather out of the mixing tank 71, that is downwardly in accordance with the illustration in FIG. 22 or FIG. 24. The rotor 2 is then placed into the inner space of the bucket 75 and the stator 3 is arranged around the bucket 75.

The invention claimed is:

1. An electromagnetic rotary drive, comprising:
a magnetically contactlessly drivable rotor free of coils, the rotor comprising a magnetically active core and being free of permanent magnets; and
a stator configured as a bearing and drive stator configured to drive the rotor magnetically and contactlessly about an axis of rotation,
the rotor capable of being supported magnetically contactlessly with respect to the stator in an operating state, and the stator comprising an upper stator part having a plurality of pronounced upper poles configured to carry upper windings and a lower stator part having a plurality of pronounced lower poles configured to carry lower windings, the upper stator part and the lower stator part being arranged spaced apart from one another with respect to an axial direction and a permanent magnet being disposed between the upper stator part and the lower stator part.

2. A rotary drive in accordance with claim 1, wherein the upper stator part comprises exactly three upper poles or the lower stator part comprises exactly three lower poles.

3. A rotary drive in accordance with claim 1, wherein a number of the upper poles is equal to a number of the lower poles.

4. A rotary drive in accordance with claim 3, wherein the upper stator part and the lower stator part form an angle therebetween with respect to the axis of rotation so that, when viewed in the axial direction, the upper poles are each arranged in a gap between two adjacent lower poles, with the angle being 360° divided by a total number of upper and lower poles.

5. A rotary drive in accordance with claim 3, wherein a number of the upper poles and a number of the lower poles is an even number, with the upper poles and the lower poles being arranged so as to overlap when viewed in the axial direction.

6. A rotary drive in accordance with claim 1, wherein the rotor comprises at least one impeller configured to convey fluids.

7. A rotary drive in accordance with claim 1, wherein the rotor is one of at least two separate rotors, each rotor of the at least two separate rotors being magnetically contactlessly drivable and free of coils, the rotors being arranged spaced apart from one another and coaxially with respect to the axial direction in the operating state, and the stator is a first stator of at least two stators, a second stator of the at least two stators being a bearing and drive stator, and comprising an upper stator part having a plurality of pronounced upper poles configured to carry upper windings and a lower stator part having a plurality of pronounced lower poles configured to carry lower windings, the upper stator part and the lower stator part of the first and second stators being arranged spaced apart from one another with respect to the axial direction, and a first permanent magnet being disposed between the upper stator part and the lower stator part of the first stator and a second permanent magnet being disposed between the upper stator part and the lower stator part of the second stator, and the first and second stators are arranged spaced apart from one another with respect to the axial direction in the operating state.

8. A rotary drive in accordance with claim 1, wherein the magnetically active core of the rotor has a plurality of pronounced rotor poles facing the poles of the stator in the operating state.

9. A rotary drive in accordance with claim 8, wherein the poles of the rotor are configured or arranged asymmetrically such that positions of engagement with respect to the stator are avoided in the operating state.

10. A rotary drive in accordance with claim 8, wherein the magnetically active core of the rotor has a ring shape, with a peripheral ring of constant diameter formed at a center with respect to the axial direction and with the poles of the rotor being disposed above and beneath the ring peripheral.

11. A rotary drive in accordance with claim 1, further comprising a coil arranged as a winding on each upper pole and each lower pole, and for each coil, a separate power amplifier is disposed such that coil current or coil voltage for the coil can be regulated independently of the coil current or the coil voltage of each other coil.

12. A rotary drive in accordance with claim 1, further comprising a coil arranged as a winding on each upper pole and each lower pole, two coils being connected together to an electrical phase, and a separate power amplifier is provided for the electrical phase.

13. A rotary drive in accordance with claim 1, wherein the permanent magnet has disk shape or a ring shape, is magnetized in the axial direction and connects the upper stator part to the lower stator part.

14. A rotary drive in accordance with claim 1, wherein the rotary drive is a pumping or mixing apparatus configured to convey or mix fluid substances or is a component of a pumping or mixing apparatus configured to convey or mix fluid substances.

15. A rotary drive in accordance with claim 1, wherein the stator is disposed radially inwardly of the rotor.

16. A rotary drive in accordance with claim 1, wherein the magnetically contactlessly drivable rotor is electrically contactless.

\* \* \* \* \*